United States Patent
Shuman et al.

(10) Patent No.: US 6,787,341 B2
(45) Date of Patent: Sep. 7, 2004

(54) PHARMACOLOGICAL TARGETING OF BACTERIAL DNA LIGASE FOR TREATMENT AND PREVENTION OF BACTERIAL INFECTIONS

(75) Inventors: Stewart Shuman, New York, NY (US); Verl Sriskanda, Valley Cottage, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 2 days.

(21) Appl. No.: 10/179,784

(22) Filed: Jun. 24, 2002

(65) Prior Publication Data

US 2003/0036647 A1 Feb. 20, 2003

Related U.S. Application Data

(60) Provisional application No. 60/300,727, filed on Jun. 25, 2001.

(51) Int. Cl.[7] .............................. C12N 9/00; C07K 1/00
(52) U.S. Cl. ...................... 435/183; 435/191; 435/440; 435/69.2; 536/23.1; 536/23.2; 530/350
(58) Field of Search ................................ 435/183, 194, 435/191, 440, 69.2; 530/350; 536/23.1, 23.2

(56) References Cited

PUBLICATIONS

Ngo et al., Computational Complexity, Protein Structure Prediction, and the Levinthal Paradox, In The Protein Folding Problem and Tertiary Structure Prediction, 1994, Merz et al. (ed.), Birkhauser, Boston, MA, pp. 433 and 492–495.*

Sriskanda, V. et al. *Conserved Residues in Domain Ia Are Required for the Reaction of Escherichia coli DNA Ligase with NAD⁺: The Journal of Biological Chemistry*, vol. 277, No. 12, Mar. 22, 2002, pp. 9695–9700.

Sriskanda, V. et al. *NAD⁺ –dependent DNA Ligase Encoded by a Eukaryotic Virus. The Journal of Biological Chemistry* vol. 276, No. 39, Sep. 28, 2001, pp. 36100–36109.

Kaczmarek F. et al. *Cloning and Functional Characterization of an NAD⁺ –Dependent DNA Ligase from Staphylococcus aureus. Journal of Bacteriology*, vol. 183, No. 10, 2001, pp. 3016–3024.

* cited by examiner

*Primary Examiner*—Richard Hutson
(74) *Attorney, Agent, or Firm*—Benjamin Aaron Adler

(57) ABSTRACT

This invention provides methods for the discovery of molecules that target an essential step of bacterial DNA replication—the sealing of DNA strands by $NAD^+$-dependent DNA ligase. Specific structural components of $NAD^+$-dependent DNA ligase that are important for the reaction of DNA ligase with $NAD^+$ and that comprise a putative binding site for the NMN component of $NAD^+$ were identified. The invention also includes recombinant DNA ligase enzymes that are defective in their reaction with $NAD^+$, but active in the ligation of pre-adenylated DNA nicks. An underlying principle of this invention is the use of $NAD^+$-reactive and $NAD^+$-defective ligases to identify molecules that specifically bind to the $NAD^+$-binding site of DNA ligase and thereby interfere with the reaction of DNA ligase with $NAD^+$.

2 Claims, 24 Drawing Sheets

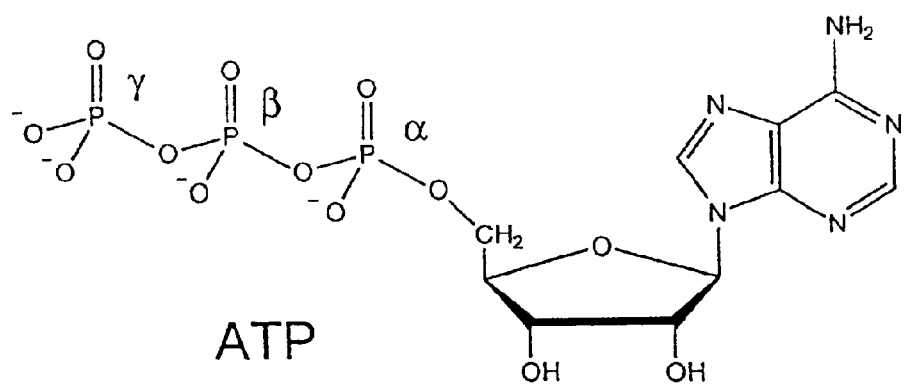
ATP
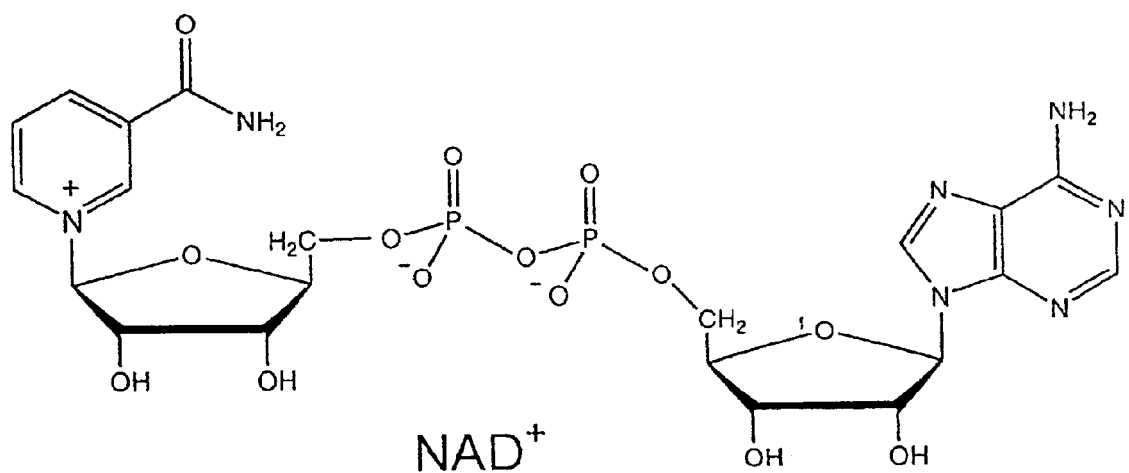
NAD⁺
Fig. 2

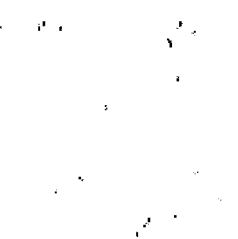
Fig. 5A

```
CATATCCGTGTCGCCCTT pATTCCGATAGTGACTACA   (SEQ ID NO: 34)
GTATAGGCACAGCGGGAA--TAAGGCTATCACTGATGT   (SEQ ID NO: 35)
```

```
            Ap
CATATCCGTGTCGCCCTT pATTCCGATAGTGACTACA (SEQ ID NO: 34)
GTATAGGCACAGCGGGAA--TAAGGCTATCACTGATGT (SEQ ID NO: 35)
```

```
               Ap
CATATCCGTGTCGCCCTT pATTCCGATAGTGACTACA (SEQ ID NO: 34)
GTATAGGCACAGCGGGAA--TAAGGCTATCACTGATGT (SEQ ID NO: 35)
```

```
AmEPV  NDLENIIQTLDNSYYDKEA-LISDKKYD-LIRNF--INNKYPN----ESLCKKIGYTPED  (SEQ ID No. 5)
MsEPV  EDISEIKILNEKYYEGET-LISDEIYDKII-EY---VNKKYPD----NDITKKIGYEPKN  (SEQ ID No. 6)
Aae    EDLREVIRYHDYKYYVEANPVIRDYDYDRLFRALKEIEKKYPELITPDSPTQRVASEISG  (SEQ ID No. 7)
Bbu    ADLKKLIRKWDKEYYVDSLPSVEDFVYDKHILRLQELESKYPEYKTLDSPTLKFGSDLLN  (SEQ ID No. 8)
Bpe    ARLRAEIEQHNIRYYVHDDPSVPDAEYDALMRDLQALEAEHPELVTPDSPTQRVGAAPLA  (SEQ ID No. 9)
Cje    LEKVALANLMMRAAYYEKDEPLASDEEYDALIRELRVFEEQNKDEISKDSPTQKIAPTIQS (SEQ ID No. 10)
Cpn    LALCRELEDHDYSYYVLHRPRISDYEYDMKLRKLLEIERSHPEWKVLWSPSTRLGDRPSG  (SEQ ID No. 11)
Ctr    IALCTELVEHDRRYYVLNQPTISDYSYDVKMRELQEIEVQHPEWKVSWSPTMYLGDRPSG  (SEQ ID No. 12)
Dra    LALRDEVALHNRAYYEQDAPTIEDDEYDRLARELRELEAAHPEFADDHSPVQTVGGAPSS  (SEQ ID No. 13)
Eco    TELRTTLRHHEYISYHVMDAPEIRDAEYDRLMRELRELETKHPELITPDSPTQRVGAAPLA (SEQ ID No. 14)
Gsu    AALRTELERHNRLYXAEDRPEITEAEYDLLFRELVDLETRFPDLAAPDSPTQRVGGAPLD  (SEQ ID No. 15)
Hin    DNLRKTLRQYEYEDHIVLDNPSVPDSEYDRLFHQLKALELEHPEFLTSDSPTQRVGAKPLS (SEQ ID No. 16)
Lla    KELTEKLNQYAYEQYTLDEPSVEDSEYDRLYQELVKLEAENPQLTRADSPTHRTGGVILD  (SEQ ID No. 17)
Lpn    ETLKEQIRKYDYHYYVLDEPIVRDAEYDRCFKALQQYEEQYPQFLSPDSPTQRVSGTPSD  (SEQ ID No. 18)
Mge    QQLVNLIKNYDYHYYVLSEPLIDDFEYDMLYKSLQQLEKDHPDLIQIDSPTQRVGGEAVK  (SEQ ID No. 19)
Mle    RKLTEEVREHQFRYYYVRDAPIISDAEFDALLDRLTVLEEQHPELCTPDSPTQLVGGAGFM (SEQ ID No. 20)
Mpn    RAIVEQLKRYDYHYYVLDDPLVSDFEYDQLYKQLQALEQAHPELIQPDSPTQRVGIVVE   (SEQ ID No. 21)
Mtu    QALAEEVREHQFRYAYEYYTLDAPSVPDAEYDELLRRLEALEEQHPELRTPDSPTQLVGAGFA (SEQ ID No. 22)
Nme    CRLTDLLNRYAYEYYTLDAPSVPDAEYDKLFREEASLETEHPEFLTADSPTQKVGAALS   (SEQ ID No. 23)
Pha    NHLRIILEQHNYNYYVLDTPSIPDSEYDRLLRELSALETEHPEFLTADSPTQRVGGAALS  (SEQ ID No. 24)
Ppu    LELRAELDQHNYRYYVLDEPSVPDAEYDRLFNELKALEAEHPHLVTPDSPTQRVGAALA   (SEQ ID No. 25)
Rma    ARLREVLNQYAYRYYVLDNPLIPDADYDLLMQALRKLEARFPELVTPDSPTVRVGGPPLG  (SEQ ID No. 26)
Rpr    KELADKIAMYNHAYYNHAYYIEDNPLVSDSEYDQLFNINLKLENTFPHLVLSNSPSKKVGANITN (SEQ ID No. 27)
Sau    NELHDLLNQYSYEYYVEDNPSVPDSEYDKLLHELIKIEEEHPEYKTVDSPTVRVGGEAQA  (SEQ ID No. 28)
Smu    NELVQLLNQYAREYYTKDNPSVSDAEYDKLYRELVELEKEFPEDILPNSPTHRVGDLVLD  (SEQ ID No. 29)
Tfe    QQLRAELVAANNAYYREDSPTLSDAEYDARLRELRTLEDRNPWQSADSPTQRVGAAPVE   (SEQ ID No. 30)
Zmo    ERLAKLISHYDHLYHDKDNPAVPDSEYDALVLRNRRIEQFFPDLIRPDSPSKKVGSRPNS  (SEQ ID No. 31)
Bst    AELRELLNRYGYEYYVLDRPSVPDAEYDRLMQELIAIEEQYPELKTSDSPTQRIGGPPLE  (SEQ ID No. 32)
Tfi    NELRDLLIRYHNYRYYVLADPEISDAEYDRLLRELKELEERFPEFKSPDSPTEQVGARPLE (SEQ ID No. 33)
```

Fig. 11

PHARMACOLOGICAL TARGETING OF BACTERIAL DNA LIGASE FOR TREATMENT AND PREVENTION OF BACTERIAL INFECTIONS

CROSS-REFERENCE TO RELATED APPLICATION

This non-provisional patent application claims benefit of provisional patent application U.S. Ser. No. 60/300,727, filed Jun. 28, 2001, now abandoned.

FEDERAL FUNDING LEGEND

This invention was produced in part using funds obtained through Grant GM63611 from the National Institutes of Health. Consequently, the federal government has certain rights in this invention.

BACKGROUND OF THE INVENTION

1. Field of the Invention

The present invention relates generally to the fields of biochemical pharmacology and drug discovery. More specifically, the present invention relates to discovery of compounds that inhibit bacterial $NAD^+$-dependent DNA ligase.

2. Description of the Related Art

DNA is susceptible to damage caused by errors committed during replication and by environmental factors such as radiation, oxidants, and alkylating agents. The repair and replication pathways converge on a common final step in which the continuity of the repaired DNA strand or the replicated lagging strand is restored by DNA ligase, an enzyme that converts nicks into phosphodiester bonds. Nicks are potentially deleterious lesions that, if not corrected, may give rise to double-strand breaks which are themselves overtly catastrophic if not repaired by homologous recombination or ligase-mediated non-homologous end-joining. Accordingly, a complete loss of DNA ligase function is lethal in every organism tested.

DNA ligases catalyze the sealing of 5' phosphate and 3' hydroxyl termini at nicks in duplex DNA via three sequential nucleotidyl transfer reactions. In the first step, attack on the α phosphorus of ATP or $NAD^+$ by ligase results in release of pyrophosphate or nicotinamide mononucleotide (NMN) and formation of a covalent intermediate (ligase-adenylate) in which AMP is linked via a phosphoamide bond to lysine. In the second step, the AMP is transferred to the 5' end of the 5' phosphate-terminated DNA strand to form DNA-adenylate (AppN). In the third step, ligase catalyzes attack by the 3' OH of the nick on DNA-adenylate to join the two polynucleotides and release AMP (FIG. 1).

DNA ligases are grouped into two families, ATP-dependent ligases and $NAD^+$-dependent ligases, according to the cofactor required for ligase-adenylate formation (1). The structures of ATP and $NAD^+$ are depicted in FIG. 2. The ATP-dependent DNA ligases are found in eubacteria, bacteriophages, archaea, eukarya, and eukaryotic viruses. ATP-dependent ligases are exemplified by the bacteriophage T7 and Chlorella virus enzymes, for which atomic structures have been solved by X-ray crystallography (2, 3). The viral ATP-dependent enzymes consist of a ~200 amino acid N-terminal nucleotidyl transferase domain and a 100-amino acid C-terminal OB-fold domain (FIG. 3). Within the N-terminal domain is an adenylate binding pocket composed of five motifs (I, III, IIIa, IV, and V) that define the polynucleotide ligase/mRNA capping enzyme superfamily of covalent nucleotidyl transferases (4). Motif I (KxDG) contains the lysine nucleophile to which AMP become covalently linked in the first step of the ligase reaction (3, 5). Motifs III, IIIa, IV, and V contain conserved side chains that contact AMP and are essential for the nucleotidyl transfer reactions (2, 3, 6). The C-terminal OB-fold consists of a five-stranded antiparallel β barrel and an α helix. The OB-fold domain includes nucleotidyl transferase motif VI, which contacts the β and γ phosphates of the NTP substrate (7) and which is uniquely required for step 1 of the ligase reaction (8).

The $NAD^+$-dependent DNA ligases have been described only in eubacteria. Genes encoding $NAD^+$-dependent ligases have been identified and sequenced from at least 60 eubacterial species. Every bacterial species encodes at least one $NAD^+$-dependent DNA ligase (referred to as LigA). The $NAD^+$-dependent DNA ligase LigA is essential for growth of *E. coli, Salmonella typhimurium, Bacillus subtilis* and *Staphylococcus aureus* (9–13). It is reasonable to think that LigA will be essential for growth of all bacteria. $NAD^+$-dependent LigA enzymes are of fairly uniform size (647 to 841 amino acids) and there is extensive amino acid sequence conservation throughout the entire lengths of the polypeptides. The atomic structures of $NAD^+$-dependent LigA enzymes of two species of thermophilic eubacteria (*Bacillus stearothermophilus* and *Thermus filiformis*) have been determined by X-ray crystallography (14, 15). The structure of full-length Tfi LigA reveals that $NAD^+$-dependent enzymes contain a catalytic core composed of nucleotidyl transferase and OB-fold domains (FIG. 3). Although there is scant amino acid sequence similarity between $NAD^+$ and ATP ligases, the tertiary structures of the catalytic cores are quite well conserved and the adenylate binding pocket of $NAD^+$ ligases is composed of the same five nucleotidyl transferase motifs described originally in the ATP-dependent enzymes. The nucleotidyl transferase motifs of the $NAD^+$-dependent ligases are highlighted in FIG. 4. A notable distinction between ATP and $NAD^+$ ligases is that the $NAD^+$ enzymes lack a recognizable counterpart of nucleotidyl transferase motif VI within their OB-fold domain. The catalytic core of Tfi ligase is flanked by a 73-amino acid N-terminal domain (Ia) and three C-terminal domains: a tetracysteine domain that binds a single Zn atom, a helix-hairpin-helix domain (HhH), and a BRCT domain (named after the C-terminus of the breast cancer gene product BRCA1).

No $NAD^+$-dependent DNA ligase activity has been identified from an eukaryotic cellular source. However, recent reports of the genomic DNA sequences of two insect poxviruses—*Melanoplus sanguinipes* entomopoxvirus and *Amsacta moorei* entomopoxvirus—identified an open reading frame in each virus that encodes a polypeptide resembling the eubacterial $NAD^+$-dependent DNA ligases (16, 17). Alignment of the 532-aa AmEPV ligase-like protein to the Tfi, Bst, and Eco LigA enzymes reveals conservation of domain Ia, the nucleotidyl transferase domain (including the five catalytic motifs) and the OB-fold (FIG. 4) as well as the HhH domain (not shown). However, the AmEPV protein lacks the Zn finger and the BRCT domains that are present in all bacterial $NAD^+$-dependent LigA enzymes. Given that individual cysteine of the Zn finger have been shown to be essential for the nick joining activity of bacterial ligases (18, 19), and the hypothesis that the BRCT domain plays an important role in DNA binding (1), it is of considerable interest to evaluate whether the insect poxvirus gene product is a DNA ligase and whether it uses $NAD^+$ as a cofactor.

$NAD^+$-dependent DNA ligases are attractive targets for drug discovery. $NAD^+$-dependent ligases are present in all bacteria and are essential for bacterial growth in all cases studied. Moreover, they are structurally conserved among bacteria, but display unique substrate specificity and domain architecture compared to ATP-dependent DNA ligases. Therefore, inhibitors of bacterial NAD$^+$-dependent DNA ligases would be outstanding candidates for effective broad spectrum antibiotic therapy.

A plausible strategy for drug discovery is to identify the structural components of bacterial NAD$^+$-dependent DNA ligase that interact with the NAD$^+$ substrate and then to isolate small molecules that recognize these components and thereby block the binding of NAD$^+$ to bacterial DNA ligase. The drug-binding site on the NAD$^+$ ligase would ideally be unique to, and conserved among, NAD$^+$ ligases, but absent from ATP-dependent ligases. The prior art is deficient in methods of executing this strategy because structural components of bacterial ligase that interact specifically with NAD$^+$ are not known. The present invention fulfills this longstanding need in the art.

SUMMARY OF THE INVENTION

The present invention is directed to the identification of compounds that inhibit bacterial growth by inhibiting the functions of bacterial NAD$^+$-dependent DNA ligase. Specific structural components within structural domain Ia of NAD$^+$-dependent DNA ligase that are important for the reaction of DNA ligase with NAD$^+$ and that comprise a putative binding site for the NMN moiety of the NAD$^+$ substrate are identified.

DNA molecules and expression vectors encoding DNA ligase enzymes that are defective in their reaction with NAD$^+$, but are active in the ligation of pre-adenylated DNA nicks are disclosed herein. The present invention also includes host cells containing these expression vectors as well as isolated recombinant DNA ligase enzymes that are defective in their reaction with NAD$^+$, but active in the ligation of pre-adenylated DNA nicks. These defective DNA ligases are termed NAD$^+$-defective ligases.

The present invention also discloses methods of screening for compounds that bind to the NAD$^+$ substrate recognition site of NAD$^+$-dependent DNA ligase or compounds that inhibit the enzymatic activities of NAD$^+$-dependent DNA ligase.

BRIEF DESCRIPTION OF THE DRAWINGS

FIG. 2 shows the structures of ATP and NAD$^+$. NAD$^+$ and ATP share a common AMP core. However, NAD lacks the γ phosphate present in ATP and instead has a nicotinamide nucleoside.

FIG. 5 shows purification and activity of wild-type AmEPV ligase and motif I mutants. FIG. 5A: Aliquots (4 μg) of the phosphocellulose preparations were analyzed by SDS-PAGE. Polypeptides were visualized by staining the gel with Coomassie brilliant blue dye. A photograph of the stained gel is shown. The positions and sizes (in kDa) of marker proteins are indicated on the left.

Duplicate reactions were resolved by SDS-PAGE and the polypeptides were transferred to a PVDF membrane (Bio-Rad) and was stained as described (28). Slices containing individual proteolytic products denoted by arrows were excised. Automated sequencing of the immobilized polypeptide was performed using an Applied Biosystems model 477A microsequencer. The N-terminal sequences are denoted in single-letter code.

Figures 8A, 8B:
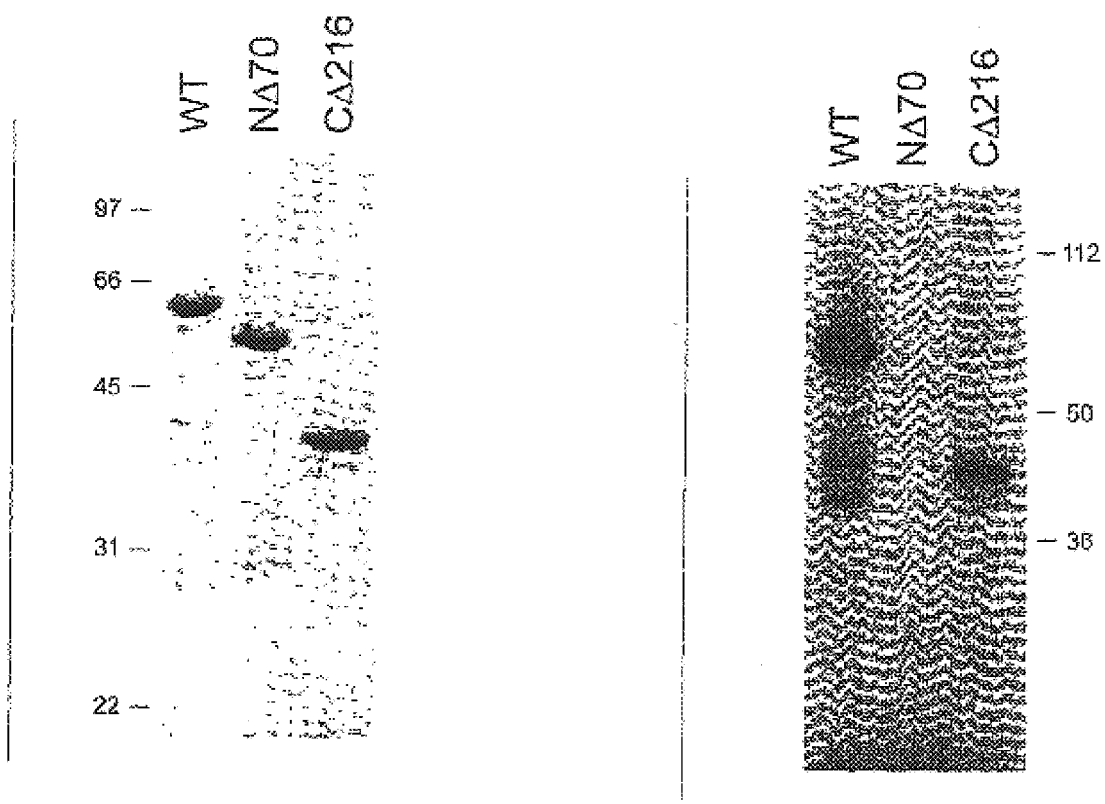
Figure 8C:
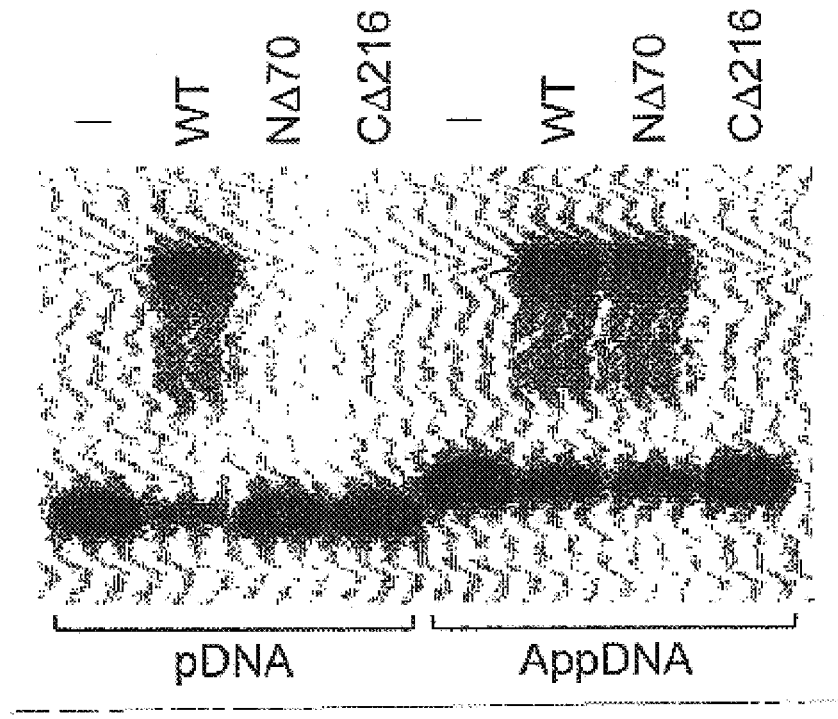

FIG. 8 shows that domain Ia is essential for AMP transfer from $NAD^+$ but not for phosphodiester synthesis at a preadenylated nick. Truncated derivatives of AmEPV ligase deleted for motif Ia (NΔ70) or for the OB and HhH domains (CΔ216) were purified by Ni-agarose and phosphocellulose column cheomtography. FIG. 8A: Aliquots (3 μg) of full-sized AmEPV ligase (WT), NΔ70, and CΔ216 were analyzed by SDS-PAGE. A Coomassie blue-stained gel is shown. The positions and sizes (in kDa) of marker proteins are indicated on the left. FIG. 8B: Ligase adenylation reaction mixtures (20 μl) containing 50 mM Tris-HCl (pH 7.5), 5 mM DTT, 5 mM $MgCl_2$, 1 μM [α-$^{32}$P]$NAD^+$ and 8 pmol of WT AmEPV ligase, NΔ70, or CΔ216 were incubated for 15 min at 22° C. The reaction products were resolved by SDS-PAGE and visualized by autoradiography. The positions and sizes (in kDa) of marker proteins are indicated on the right. FIG. 8C: Ligation of nicked DNA and nicked DNA-adenylate. Reaction mixtures (20 μl) containing 50 mM Tris-HCl (pH 7.5), 10 mM $(NH_4)_2SO_4$, 5 mM DTT, 5 mM $MgCl_2$, either 200 fmol of $^{32}$P-labeled nicked DNA (pDNA) plus 50 μM $NAD^+$ or 200 fmol $^{32}$P-labeled nicked DNA-adenylate (AppDNA) and no $NAD^+$, and 2 pmol of WT AmEPV ligase, NΔ70, or CΔ216 were incubated for 30 min at 22° C. The reaction products were resolved by denaturing PAGE. An autoradiograph of the gel is shown. Control reaction mixtures lacking ligase are shown in lanes -. The nicked DNA-adenylate substrate used in the ligation reactions is illustrated at the bottom.

Figure 9A:
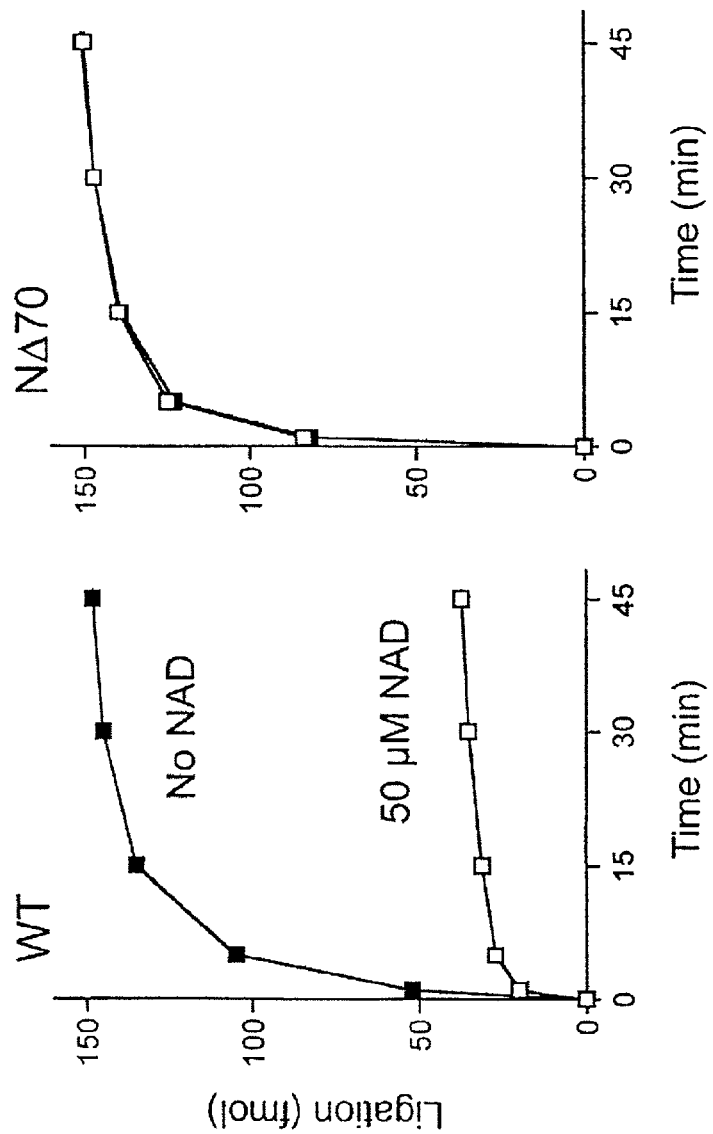
Figure 9B:
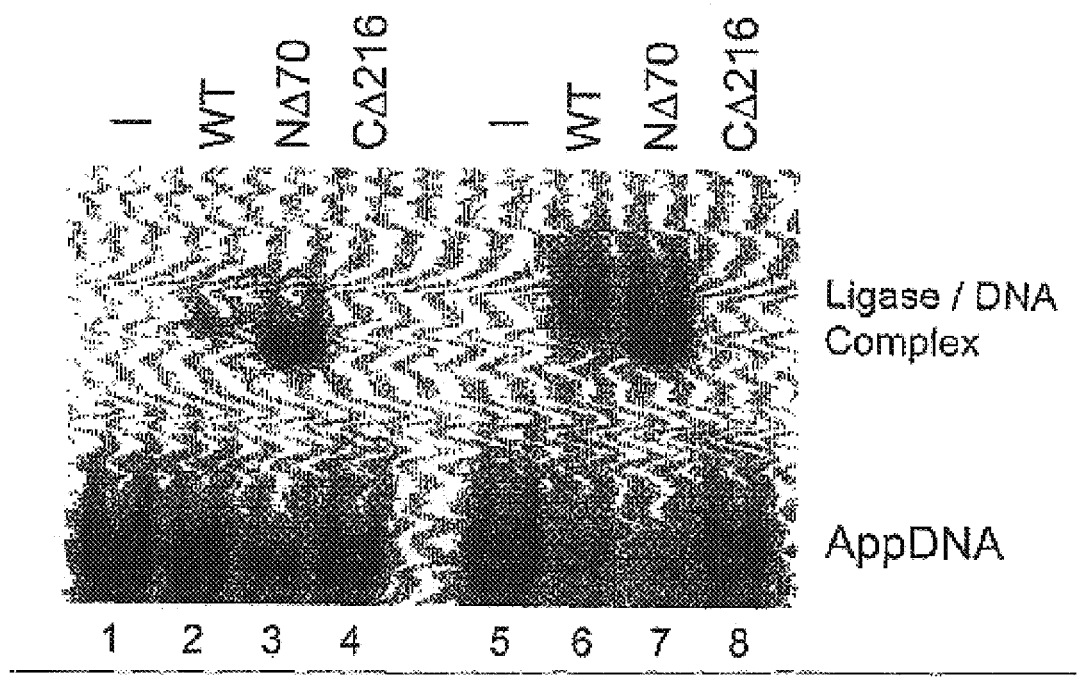

FIG. 9 shows the reaction of AmEPV ligase with nicked DNA-adenylate. FIG. 9A: Kinetic analysis of step 3. Reaction mixtures containing (per 20 μl) 50 mM Tris-HCl (pH 7.5), 10 mM $(NH_4)_2SO_4$, 5 mM DTT, 5 mM $MgCl_2$, 200 fmol of $^{32}$P-labeled nicked DNA-adenylate, 1 pmol of WT ligase or NΔ70, and either no added $NAD^+$(■) or 50 μM $NAD^+$ (□) were incubated at 22° C. The reactions were initiated by the addition of enzyme. Aliquots (20 μl) were withdrawn at 1, 5, 15, 30, and 45 min and quenched immediately with EDTA and formamide. The extents of ligation are plotted as a function of time. FIG. 9B: Effects of the NΔ70 and CΔ216 deletions on the binding of ligase to nicked DNA-adenylate. Reaction mixtures (20 μl) containing 50 mM Tris-HCl (pH 7.5), 5 mM DTT, 200 fmol of $^{32}$P-labeled nicked DNA-adenylate, and either 2 pmol (lanes 2, 3, and 4) or 4 pmol (lanes 6, 7, and 8) of WT ligase, NΔ70, or CΔ216 were incubated for 10 min at 22° C. Ligase was omitted from control reaction mixtures (lanes 1 and 5). The mixtures were adjusted to 5% glycerol and then analyzed by electrophoresis through a 5% native polyacrylamide gel containing 90 mM Tris-borate, 2.5 mM EDTA. The free nicked DNA-adenylate (AppDNA) and ligase-DNA complexes of retarded mobility were visualized by autoradiography of the dried gel.

Figure 10A:
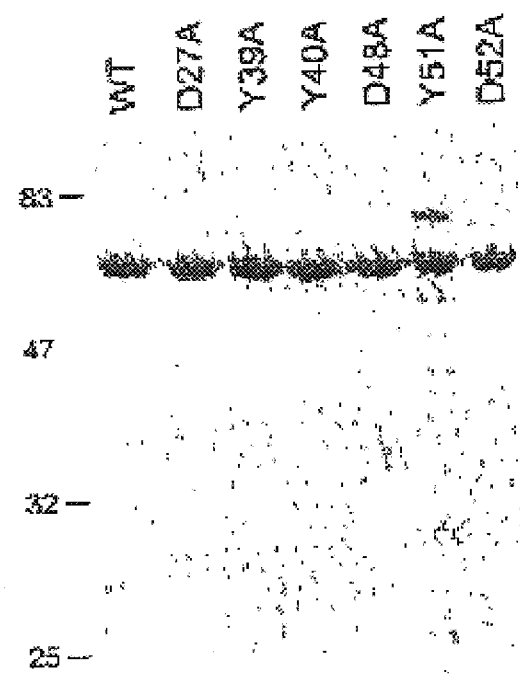
Figure 10B:
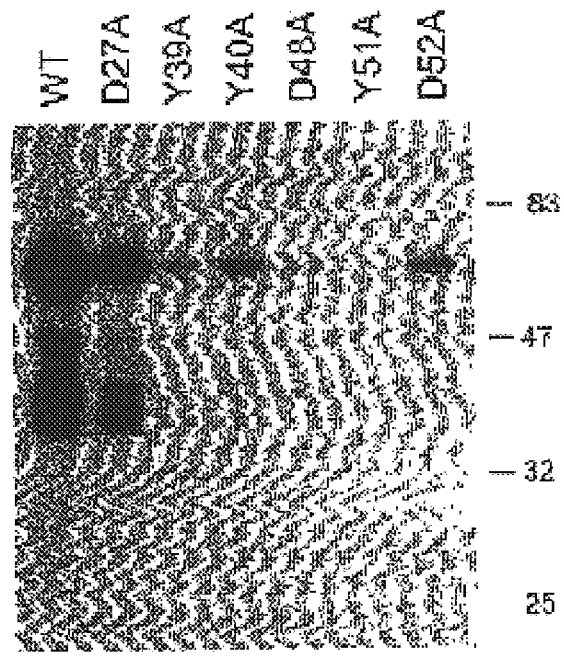
Figure 10C:
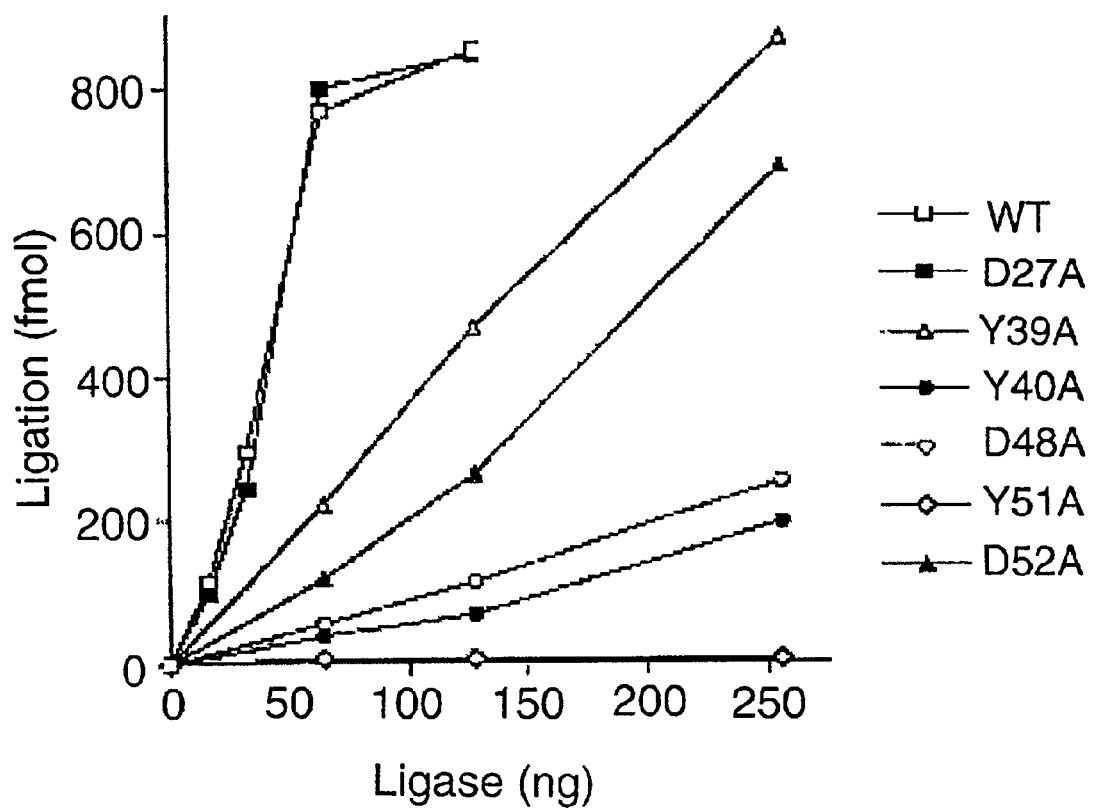

FIG. 10 shows the effects of alanine mutations in domain Ia of AmEPV ligase. FIG. 10A: Aliquots (3.5 μg) of WT AmEPV ligase and the indicated alanine mutants in domain Ia were analyzed by SDS-PAGE. A Coomassie blue-stained gel is shown. FIG. 10B: Ligase adenylation reaction mixtures (20 μl) containing 50 mM Tris-HCl (pH 7.5), 5 mM DTT, 5 mM $MgCl_2$, 1 μM [(α-$^{32}$P]$NAD^+$ and 510 ng of WT ligase or the indicated alanine mutants were incubated for 15 min at 22° C. The reaction products were resolved by SDS-PAGE and visualized by autoradiography. FIG. 10C: Nick joining reaction mixtures (20 μl) containing 50 mM Tris-HCl (pH 7.5), mM $(NH_4)_2SO_4$, 5 mM DTT, 5 mM $MgCl_2$, 50 μM $NAD^+$, 1 pmol of $^{32}$P-labeled nicked DNA, and increasing amounts of WT ligase or the indicated alanine mutants were incubated for 30 min at 22° C. The extents of ligation are plotted as a function of input protein. Each datum is the average of two titration experiments.

FIG. 11 shows the alignment of the predicted amino acid sequences of domain Ia of $NAD^+$ ligases from two entomopoxviruses AmEPV and MsEPV and 27 species of bacteria over the segment of *E. coli* DNA ligase (Eco) from residues 9 to 68. The secondary structure of Tfi ligase domain Ia is shown below the aligned sequences. The five amino acids that are conserved in all of the $NAD^+$ ligases and are defined by alanine scanning as important for the reaction of the AmEPV and *E. coli* ligases with $NAD^+$ are highlighted by shaded boxes and by dots. The bacterial ligases included in the alignment are from *Aquifex aeolicus* (Aae), *Borrelia burgdorferi* (Bbu), *Bordatella pertussis* (Bpe), *Campylobacter jejuni* (Cje), *Chlamydia pneumoniae* (Cpn) *Chlamydia trachomatis* (Ctr), *Deinococcus radiodurans* (Dra), *Escherichia coli* (Eco), *Haemophilus influenzae* (Hin), *Geobacter sulfurreducens* (Gsu), *Lactococcus lactis* (Lla), *Legionella pneumophila* (Lpn), *Mycoplasma genitalia* (Mge), *Mycobacterium leprae* (Mle), *Mycoplasma pneumoniae* (Mpn), *Mycobacterium tuberculosis* (Mtu), *Neisseria meningitidis* (Nme), *Pseudoalteromonas haloplanktis* (Pha), *Pseudomonas putida* (Ppu), *Rhodothermus marinus* (Rma), *Rickettsia prowazekii* (Rpr), *Staphylococcus aureus* (Sau), *Streptococcus mutans* (Smu), *Thiobacillus ferrooxidans* (Tfe), *Zymomonas niobilis* (Zmo), *Bacillus stearothermophilus* (Bst), and *Thermus filiformis* (Tfi).

Figure 12A:
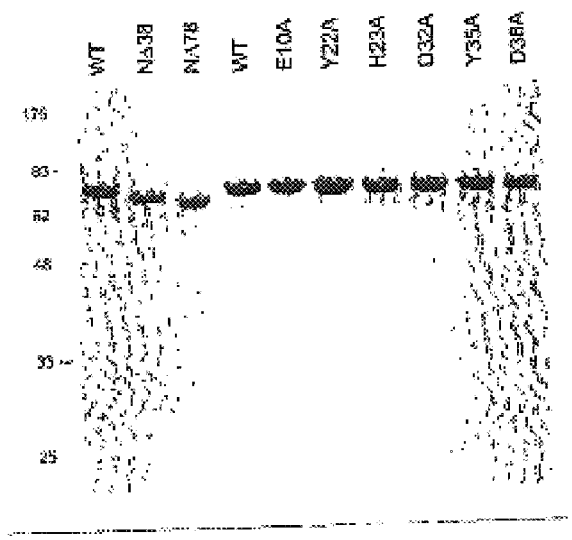
Figure 12B:
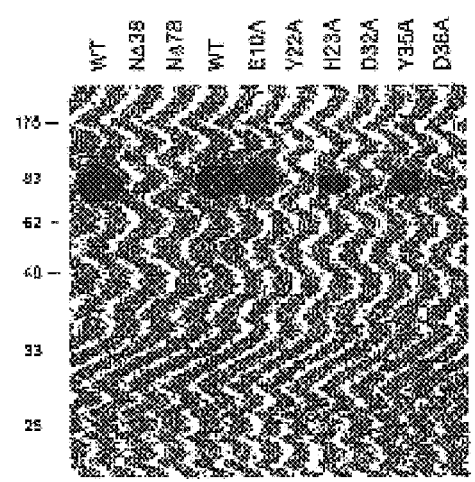
Figure 12C:
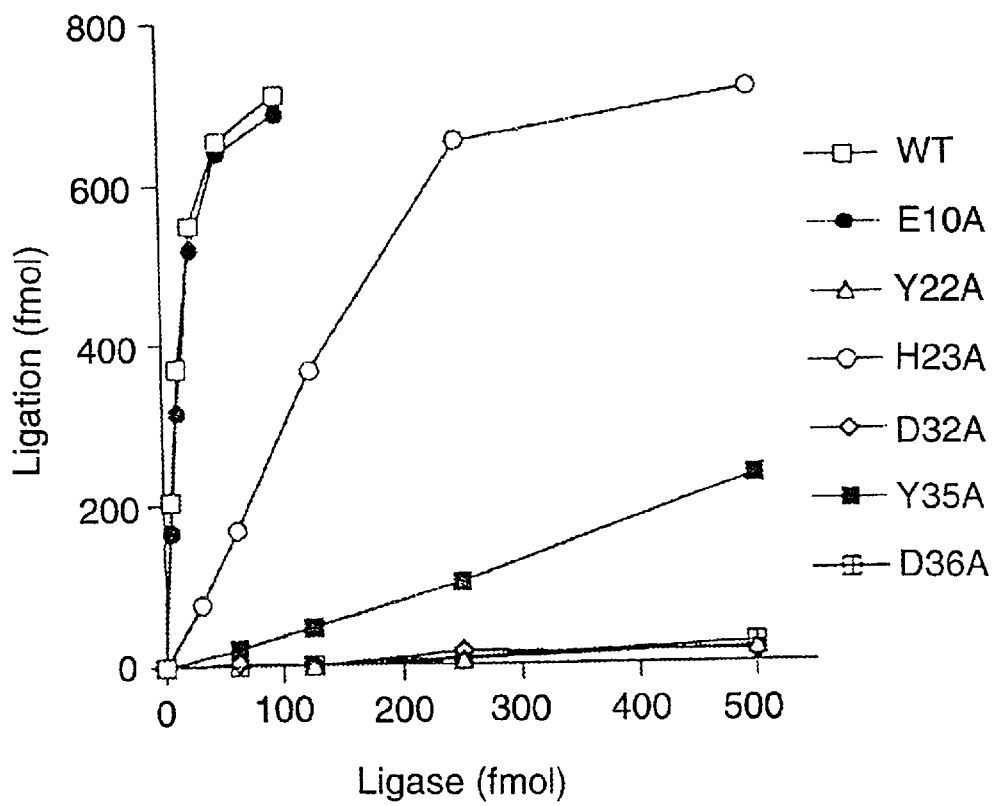

FIG. 12 shows the effects of deletion and alanine mutations in domain Ia of *E. coli* DNA ligase LigA. FIG. 12A: Aliquots (5 μg) of wild-type (WT) *E. coli* ligase, N-terminal deletion mutants NΔ38 and NΔ78, and the full-length ligase proteins containing the indicated alanine mutations in domain Ia were analyzed by SDS-PAGE. A Coomassie blue-stained gel is shown. FIG. 12B: Ligase adenylation reaction mixtures (20 μl) containing 50 mM Tris-HCl (pH 7.5), 5 mM DTT, 5 mM $MgCl_2$, 1 μM [α-$^{32}$P]$NAD^+$ and 8 pmol of WT ligase, NΔ38, NΔ78, or the indicated alanine mutants were incubated for 5 min at 37° C. The reaction products were resolved by SDS-PAGE and visualized by autoradiography. FIG. 12C: Nick joining reaction mixtures (20 μl) containing 50 mM Tris-HCl (pH 7.5), 10 mM $(NH_4)_2SO_4$, 5 mM DTT, 5 mM $MgCl_2$, 20 μM $NAD^+$, 1 pmol of $^{32}$P-labeled nicked DNA, and increasing amounts of WT ligase or the indicated alanine mutants were incubated for 10 min at 22° C. The extents of ligation are plotted as a function of input protein.

Figure 13:
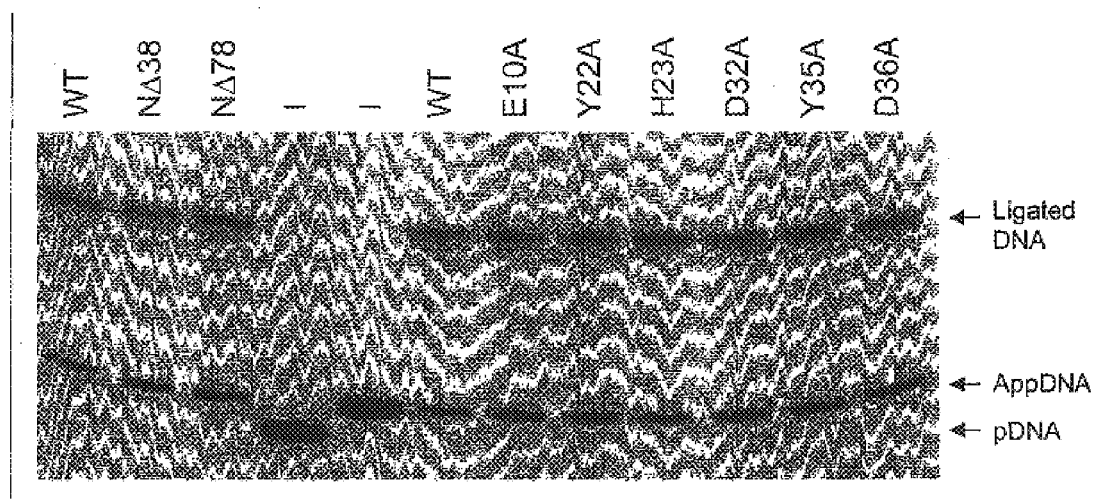

FIG. 13 shows that domain Ia is dispensable for phosphodiester synthesis at a preadenylated nick. Reaction mixtures containing 1 pmol of $^{32}$P-labeled nicked DNA-adenylate (AppDNA) and either 8 pmol of wild-type (WT) *E. coli* ligase, deletion mutants NΔ38 and NΔ78, or the full-length ligase proteins containing the indicated alanine mutations in domain Ia were incubated for 60 min at 22° C. The reaction products were resolved by denaturing PAGE. An autoradiograph of the gel is shown. Control reaction mixtures containing either $^{32}$P-labeled nicked DNA-adenylate (AppDNA) or nicked DNA (pDNA) substrates and no ligase are shown in lanes -. The positions of the pDNA, AppDNA, and ligated 36-mer DNA strands are indicated by arrows on the right. The position of the radiolabeled phosphate of AppDNA is denoted by •. The nicked DNA-adenylate substrate used in the ligation reactions is illustrated at the bottom.

FIG. 14 shows the kinetics of phosphodiester formation at a preadenylated nick. The nicked DNA-adenylate substrate is illustrated in FIG. 13. The DNA-adenylate ligation reaction mixtures (20 μl) contained 50 mM Tris-HCl (pH 7.5), 5 mM DTT, 5 mM $MgCl_2$, 200 fmol of nicked DNA-adenylate substrate, 2 pmol of wild-type or mutant EcoLigA proteins as specified were incubated at 22° C. The sealing reactions were initiated by adding ligase. Aliquots (20 μl) were withdrawn at the times specified and quenched immediately with EDTA and formamide. The products were resolved by denaturing PAGE and the extents of ligation were determined by scanning the gel with a phosphorimager. The extent of strand joining is plotted as a function of reaction time.

Figure 15A:
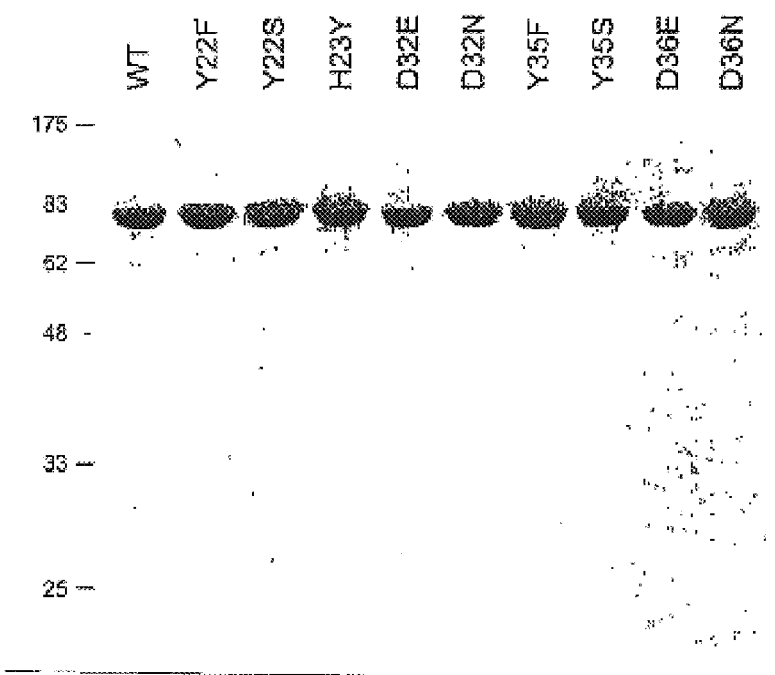
Figure 15B:
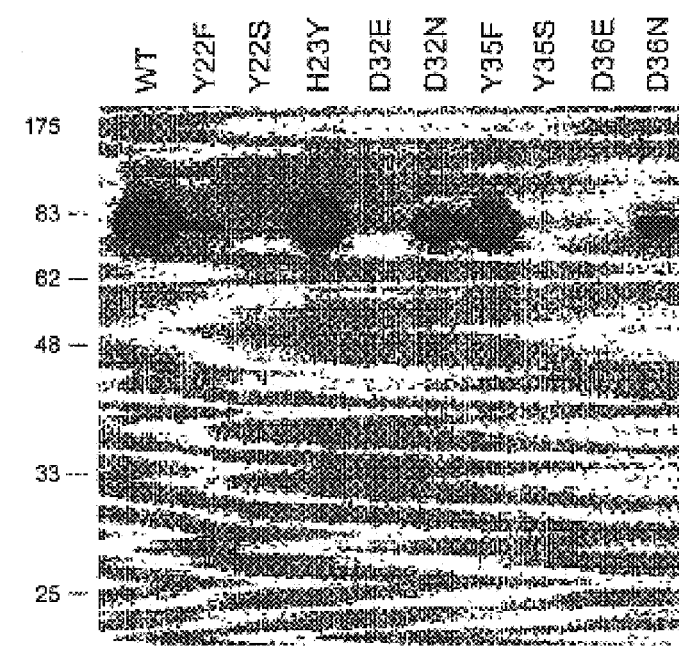

FIG. 15 shows the effects of conservative mutations in domain Ia of E. coli DNA ligase LigA. FIG. 15A: Aliquots (5 μg) of wild-type (WT) E. coli ligase and proteins containing the indicated mutations in domain Ia were analyzed by SDS-PAGE. The Coomassie blue-stained gel is shown. The positions and sizes (in kDa) of marker proteins are indicated on the left. FIG. 15B: Ligase adenylation reaction mixtures (20 μl) containing 50 mM Tris-HCl (pH 7.5), 5 mM DTT, 5 mM $MgCl_2$, 1 μM [α-$^{32}$P]NAD$^+$ and 8 pmol of WT ligase or the indicated mutants were incubated for 5 min at 37° C. The reaction products were resolved by SDS-PAGE and visualized by autoradiography.

FIG. 16 shows a kinetic analysis of Eco LigA adenylation. Reaction mixtures containing (per 20 μl) 50 mM Tris-HCl (pH 7.5), 5 mM DTT, 5 mM $MgCl_2$, 1 μM [$^{32}$P-AMP]NAD$^+$ and 8 pmol of ligase were incubated at 22° C. Aliquots (20 μl) were withdrawn at 15, 30, 60 and 120 s and then quenched immediately with SDS. The products were analyzed by SDS-PAGE. Formation of the ligase-[$^{32}$P]AMP adduct is plotted as a function of time.

FIG. 17 shows a model of nucleotide specificity in ligase-adenylation as dictated by the interactions of domain Ia (NAD$^+$ ligase) or motif IV of the OB-fold (ATP ligase) with the leaving groups of NAD$^+$ or ATP.

DETAILED DESCRIPTION OF THE INVENTION

The present invention identifies specific structural components within structural domain Ia of NAD$^+$-dependent DNA ligase that are important for the reaction of DNA ligase with NAD$^+$ and that comprise a putative binding site for the NMN moiety of the NAD$^+$ substrate. These results facilitate the discovery of drugs that target an essential step of bacterial DNA replication and repair—the sealing of newly replicated DNA strands by DNA ligase. The underlying principle of the invention is the identification and use of a structural domain of bacterial NAD$^+$-dependent DNA ligases that mediates interaction of bacterial ligases with NAD$^+$. The ligase protein, the isolated NAD$^+$-interaction domain, and mutated versions that are defective in NAD$^+$ interaction can be used to select and identify small molecule ligands that specifically bind to the NAD$^+$ site.

The methods disclosed herein test a battery of candidate molecules for their ability to bind specifically to NAD$^+$ ligase at the site that determines NAD$^+$ specificity. In one embodiment of the invention, this would entail local application of NAD$^+$ ligase or isolated NAD$^+$-interaction domain to an array of candidate molecules immobilized on beads or on a surface matrix. NAD$^+$ ligase or isolated NAD$^+$-interaction domain can be tagged with fluorescent probes or antibody epitopes to detect binding of the NAD$^+$ ligase or the isolated NAD$^+$-interaction domain to either a subpopulation of beads or loci in the matrix. These loci would contain unique molecules that specifically bind to the ligase or ligase domain. Reapplication of mutated versions of NAD$^+$ ligase or isolated NAD$^+$-interaction domain that are defective in the interaction with NAD$^+$ would then discriminate ligands that genuinely bind at the NAD$^+$ interaction site from those that bind elsewhere on the native NAD$^+$ ligase or isolated domain. For example, molecules that bind to the "wild-type" NAD$^+$ ligase or isolated NAD$^+$-interaction domain, but not to mutated versions defective in NAD$^+$ interaction would be regarded as promising leads for antibiotic drugs.

An advantage of the present invention is that it is geared to detect specific candidate drugs that interfere with NAD$^+$ recognition by ligases based on biochemically validated differences in binding to the ligases. The method is simple and adaptable to high-throughput screening for inhibitors. Once candidate molecules are identified, further examination of inhibition of strand joining reaction of NAD$^+$ ligases from bacteria of interest can occur.

The present invention is drawn to isolated DNA molecules encoding mutated NAD$^+$-dependent DNA ligase enzymes that are defective in reacting with NAD$^+$ but are active in the ligation of preadenylated DNA nicks. These DNA ligases are mutated by deleting domain Ia of these DNA ligases or by substituting one or more conserved residues in the domain Ia. Examples of these DNA molecules include, but are not limited to, DNAs that encode Amsacta moorei entomopoxvirus NAD$^+$-dependent DNA ligase comprising substitution mutation at Tyrosine-39, Tyrosine-40, Aspartate-48, and/or Aspartate-52, or Escherichia coli NAD$^+$-dependent DNA ligase comprising substitution mutation at Tyrosine-22, Histidine-23, Aspartate-32, Tyrosine-35, and/or Aspartate-36.

Expression vectors comprising DNA molecules encoding NAD$^+$-dependent DNA ligase enzymes that are defective in reacting with NAD$^+$ but are active in the ligation of preadenylated DNA nicks, host cells expressing these vectors and recombinant DNA ligases encoded by these vectors are also included in the present invention.

The present invention also provides a method of screening for compounds that bind to the NAD$^+$ substrate recognition site of NAD$^+$-dependent DNA ligase based on differential binding to wild-type and mutated NAD$^+$-dependent DNA ligase. In general, the method employs mutated DNA ligases disclosed herein.

The present invention also provides methods of screening for compounds that inhibit the enzymatic activities of NAD$^+$-dependent DNA ligase. These enzymatic activities include nucleotidyl transferase activity in the presence of NAD$^+$ and a divalent cation, and DNA ligase activity in the presence of NAD$^+$, a divalent cation, and a nicked duplex DNA substrate containing 3'—OH and 5'-PO4 termini at the nick.

It is well known in the art that the amino acid sequence of a protein is determined by the nucleotide sequence of the DNA that encodes the protein. Because of the degeneracy of the genetic code (i.e., for most amino acids, more than one nucleotide triplet (codon) codes for a single amino acid), different nucleotide sequences can code for a particular amino acid, or polypeptide. Thus, the polynucleotide sequences of the subject invention also encompass those degenerate sequences that encode the polypeptides of the subject invention, or a fragment or variant thereof. Accordingly, any nucleotide sequence (mutated from the sequences disclosed herein) which encodes the NAD$^+$-dependent and NAD$^+$-defective ligases described herein comes within the scope of this invention and the claims appended hereto.

Also, as described herein, fragments or mutated versions of NAD$^+$-dependent and NAD$^+$-defective ligase enzymes are part of the subject invention so long as such fragments or mutated versions retain biochemical properties so that such fragments or mutated versions are useful in the methods described herein. As used herein, "fragment," as applied to a polypeptide, will ordinarily be at least 10 residues, more typically at least 20 residues, and preferably at least 30 (e.g., 50) residues in length, but less than the entire, intact sequence. Fragments can be generated by methods known to those skilled in the art, e.g., by enzymatic digestion of naturally occurring or recombinant protein, by recombinant DNA techniques using an expression vector that encodes a defined fragment, or by chemical synthesis.

As used herein, "mutated version," as applied to a polypeptide, will ordinarily be an altered form of the polypeptide in which one or more amino acids are substituted by different amino acids or by modified amino acids. Mutated versions can be generated by methods known to those skilled in the art, e.g., by chemical modification of naturally occurring or recombinant protein, by recombinant DNA techniques using an expression vector that encodes a defined fragment, or by chemical synthesis. The ability of a candidate fragment or mutated version to exhibit a characteristic of the DNA ligase enzyme can be readily assessed by a person having ordinary skill in this art by using the methods described herein.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention, the sequence is given in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to DNA sequence that participates in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences that facilitate efficient transcription and translation of the inserted DNA fragment are used in connection with a host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

As used herein, the term "host" is meant to include not only prokaryotes but also eukaryotes such as yeast, plant and animal cells. A recombinant DNA molecule or gene which encodes a DNA ligase of the present invention can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. A "clone" is a population of cells derived from a single cell or ancestor by mitosis. A "cell line" is a clone of a primary cell that is capable of stable growth in vitro for many generations.

The following examples are given for the purpose of illustrating various embodiments of the invention and are not meant to limit the present invention in any fashion:

EXAMPLE 1

Expression Of AmEPV Ligase In Bacteria And Demonstration Of Ligase Activity

AmEPV open reading frame 199 encoding a ligase-like polypeptide was cloned into a T7 RNA polymerase-based bacterial expression vector so as to fuse the 532-amino acid AmEPV protein to a 20-amino acid N-terminal leader peptide containing 10 tandem histidines. The expression plasmid was introduced into *E. Coli* BL21(DE3), a strain that contains the T7 RNA polymerase gene under the control of a lacUV5 promoter. The recombinant His-tagged protein was purified from soluble extract of IPTG-induced bacteria by nickel-agarose affinity chromatography and phosphocellulose cation exchange chromatography. SDS-PAGE analysis showed that the phosphocellulose preparation was highly enriched with respect to the 62 kDa AmEPV ligase polypeptide (FIG. 5A). The identity of the 62 kDa protein was confirmed by N-terminal sequence analysis. In addition, the preparation contained a cluster of smaller polypeptides (~35–45 kDa) corresponding to N-terminal fragments of the AmEPV ligase.

Figure 5B:
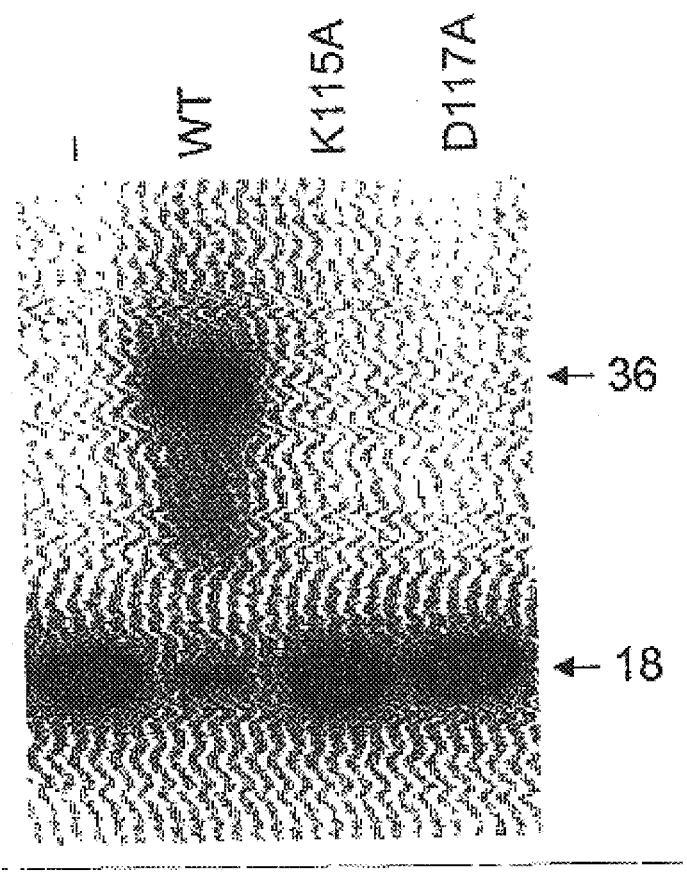
FIG. 5B shows DNA ligation. Reaction mixtures (20 μl) containing 50 mM Tris-HCl (pH 7.5), 10 mM (NH$_4$)$_2$SO$_4$, 5 mM DTT, 5 mM MgCl$_2$, 50 μM NAD$^+$, 1 pmol of $^{32}$P-labeled nicked DNA, and 260 ng of wild-type (WT) AmEPV ligase, K115A, or D117A were incubated for 30 min at 22° C. The reactions were quenched with formamide and EDTA. The reaction products were resolved by electrophoresis through a 12% polyacrylamide gel containing 7M urea in TBE (90 mM Tris-borate, 2.5 mM EDTA). An autoradiogram of the gel is shown. The positions of the input $^{32}$P-labeled 18-mer strand and the 36-mer ligated strand are indicated by arrows on the right. The nicked duplex substrate used in the ligation reactions is illustrated at the bottom.
Figure 5C:
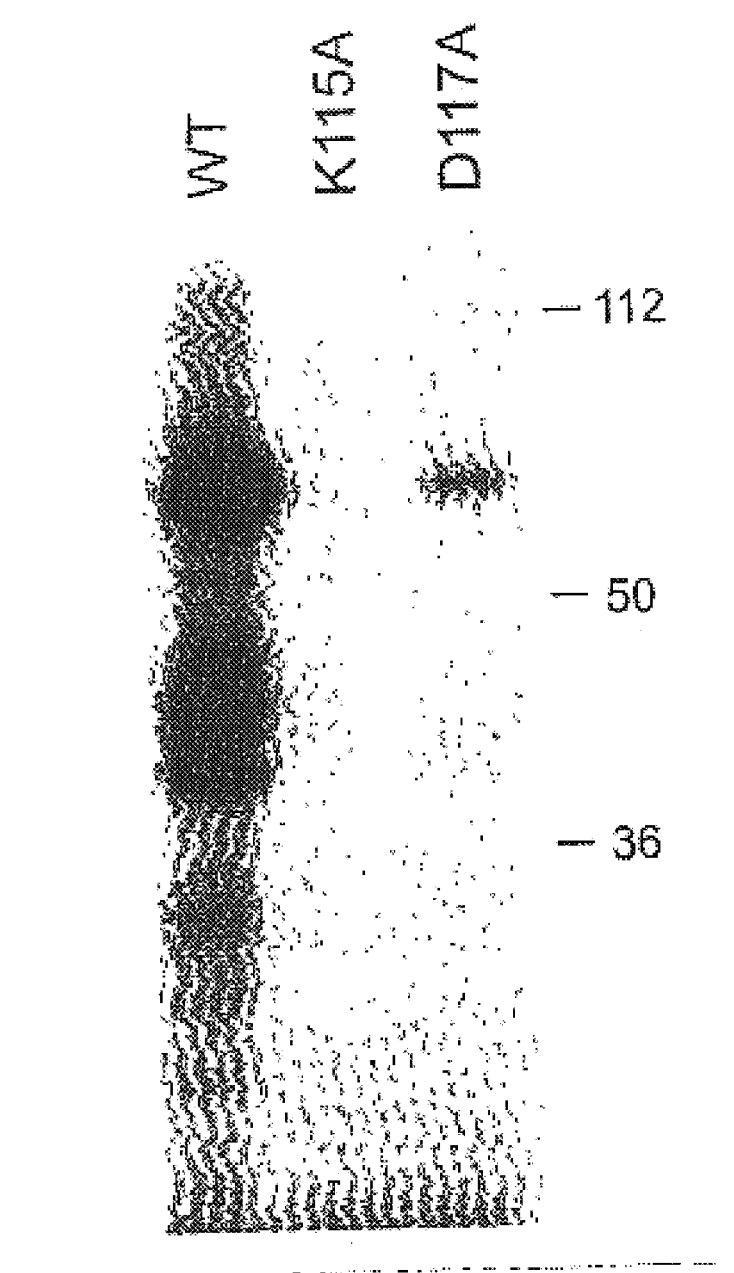
FIG. 5C shows ligase-adenylate formation. Reaction mixtures (20 μl) containing 50 mM Tris-HCl (pH 7.5), 5 mM DTT, 5 mM MgCl$_2$, 1 μM [α-$^{32}$P]NAD$^+$ and 510 ng of wild-type (WT) AmEPV ligase, K115A, or D117A were incubated for 15 min at 22° C. Reactions were quenched by adding SDS to 1%. The reaction products were resolved by SDS-PAGE. An autoradiogram of the dried gel is shown. The positions and sizes (in kDa) of marker proteins are indicated on the right.

The ability of the recombinant AmEPV protein to seal a duplex DNA substrate containing a single nick was assayed (FIG. 5C). $NAD^+$ and magnesium were included in the assay mixtures. Ligation activity was evinced by conversion of the 5'$^{32}$P-labeled 18-mer substrate to 36-mer product. More than 90% of the input nicked DNA molecules were sealed. Thus the AmEPV protein is indeed a DNA ligase.

The initial step in DNA ligation involves formation of a covalent enzyme-adenylate intermediate. In order to assay adenylyltransferase activity, the recombinant AmEPV protein was incubated with [$\alpha$-$^{32}$P]$NAD^+$ and magnesium. This resulted in the formation of a $^{32}$P-labeled covalent nucleotidyl-protein adduct that comigrated with the full-size ligase polypeptide during SDS-PAGE (FIG. 5C, lane WT). Additional labeled species were formed that corresponded to N-terminal fragments of the AmEPV ligase. This experiment shows that AmEPV ligase is active in covalent nucleotidyl transfer with $NAD^+$ as the AMP donor.

EXAMPLE 2
Effects Of Alanine Mutations In Motif I Of AmEPV Ligase

Figure 1:
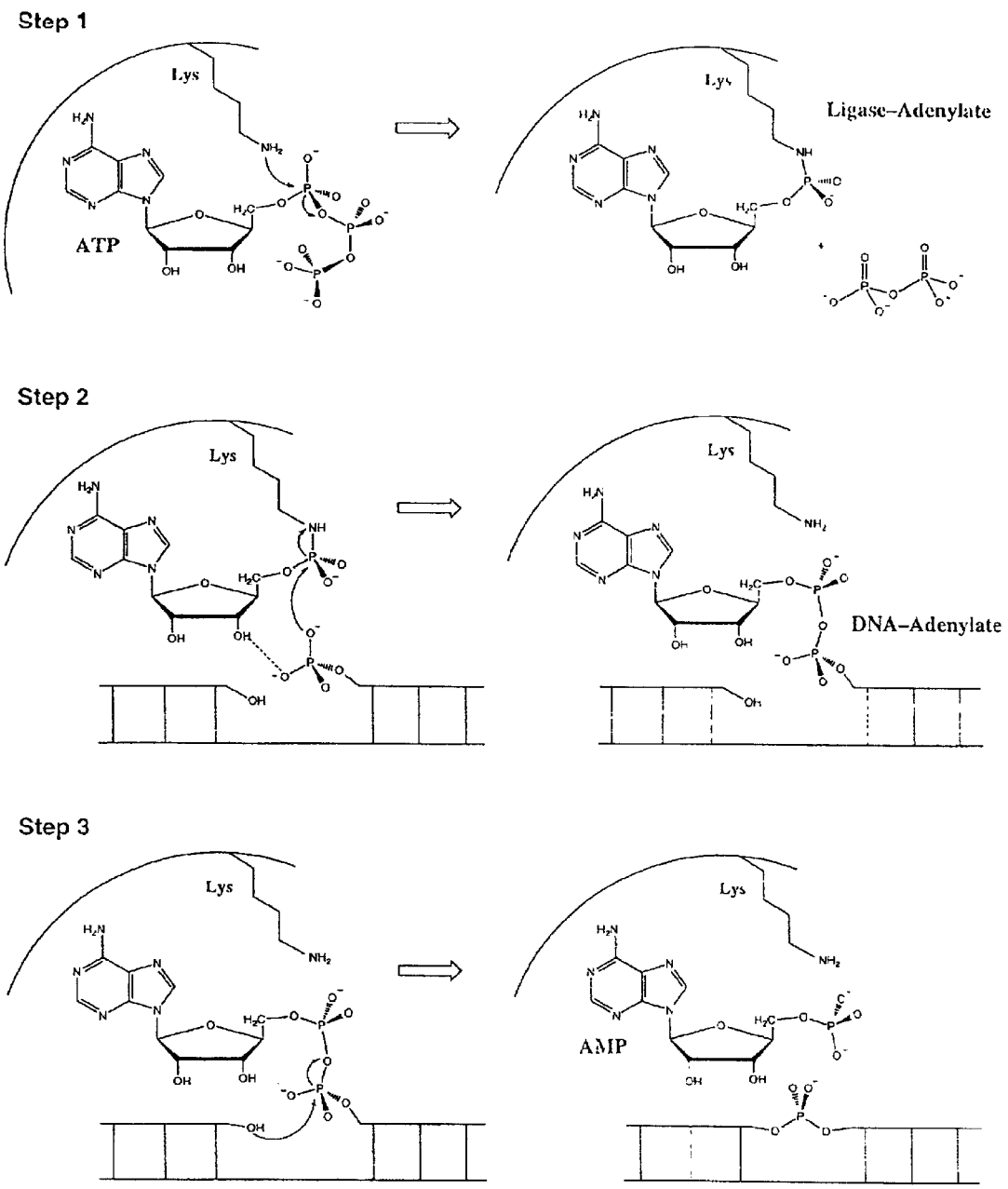
FIG. 1 shows the reaction mechanism of DNA ligases. The ligase reaction entails three sequential nucleotidyl transfer steps. In the first step, nucleophilic attack on the α phosphorus of ATP or NAD$^+$ by ligase results in release of PP$_i$ or NMN and formation of a covalent ligase-adenylate intermediate in which AMP is linked via a phosphoamide (P—N) bond to Nζ of a lysine. For simplicity, only the reaction with ATP is illustrated. In the second step, the AMP is transferred to the 5' end of the 5' phosphate-terminated DNA strand to form DNA-adenylate (AppN-). In this reaction, the 5' phosphate oxygen of the DNA strand attacks the phosphorus of ligase-adenylate and the active site lysine is the leaving group. In the third step, ligase catalyzes attack by the 3'OH of the nick on DNA-adenylate to join the two polynucleotides and liberate AMP.
Figure 3:
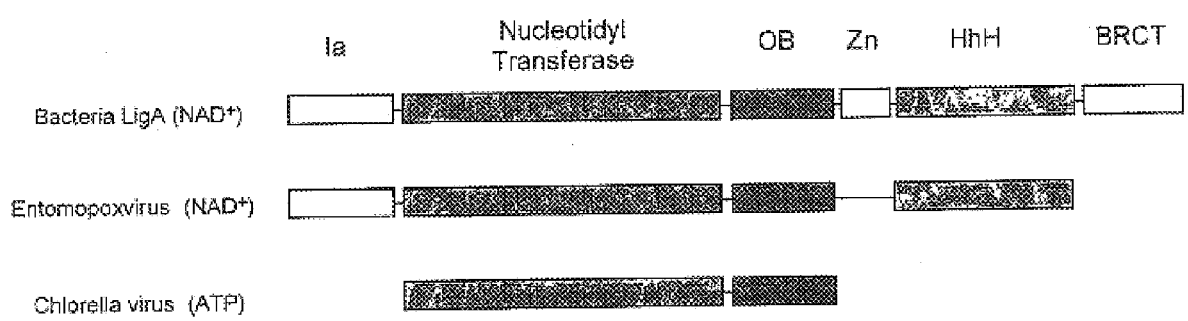
FIG. 3 shows a comparison of the domain structures of bacterial (NAD$^+$-dependent) DNA ligases (LigA enzymes), entomopoxvirus (NAD$^+$-dependent) DNA ligase, and Chlorella virus (ATP-dependent) DNA ligase.
Figure 4:
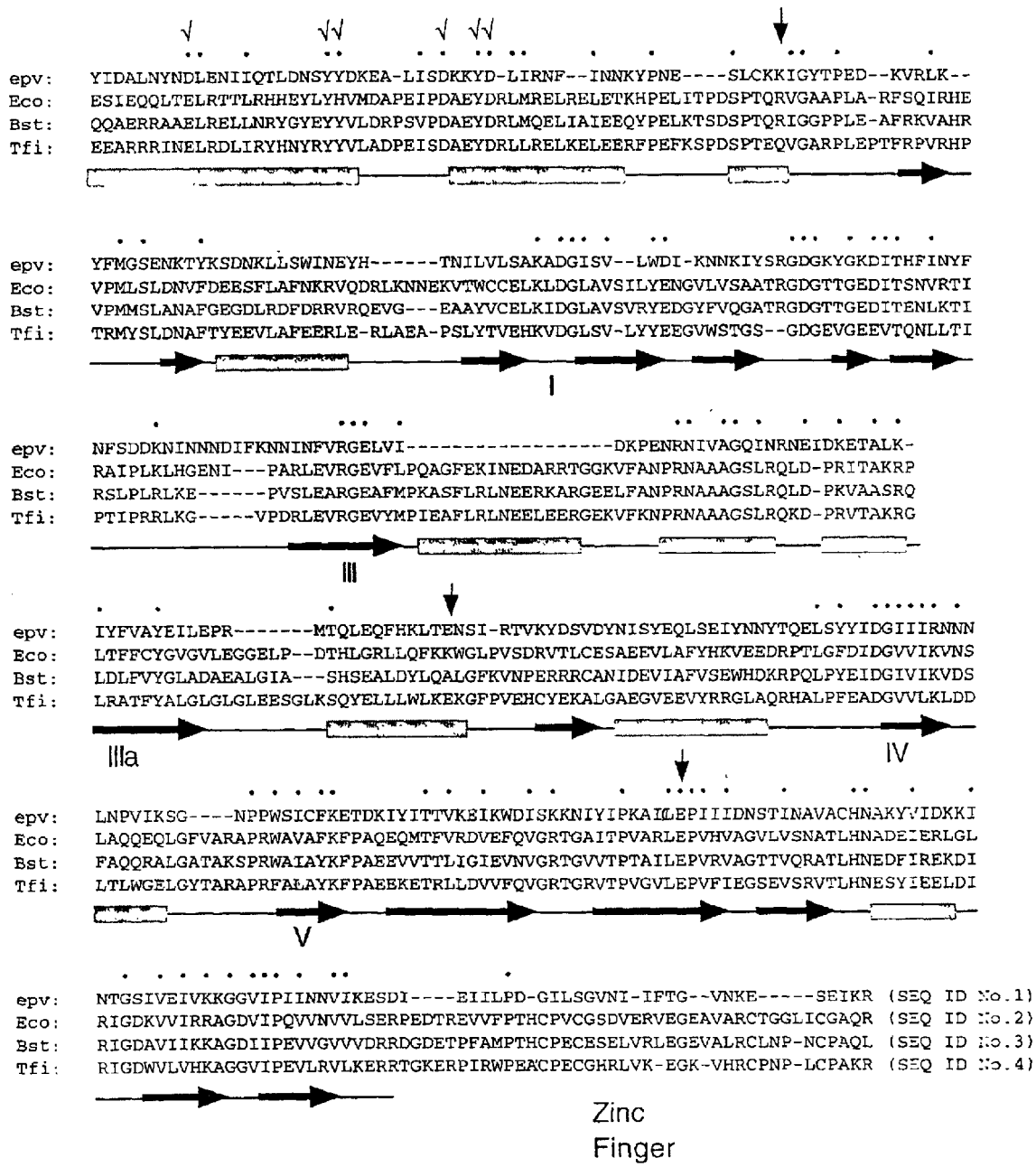
FIG. 4 shows the aligned primary structures of eubacterial NAD$^+$-dependent DNA ligases and entomopoxvirus DNA ligase. The amino acid sequence of AmEPV ligase from amino acids 19 to 395 is aligned with the N-terminal portions of the NAD$^+$-dependent ligases (LigA enzymes) encoded by E. coli (Eco), B. stearothermophilus (Bst), and T. filiformis (Tfi). The alignment encompasses the Ia, nucleotidyltransferase, OB-fold and Zn finger domains. The secondary structure of Tfi ligase is shown below the amino acid sequence. Gaps in the amino acid sequence alignment are indicated by dashes (-). Positions of side-chain conservation (identity or structural similarity) in all four proteins are denoted by dots (•) above the sequence. The conserved nucleotidyl transferase motifs are denoted below the Tfi sequence; motifs I, III, IIIa, IV, and V are highlighted in shaded boxes. The four cysteines comprising the Zn finger are located near the C-terminus of the alignment and are highlighted in shaded boxes. The sites of trypsin and V8 cleavage in native AmEPV ligase are indicated by arrows.

The KxDG sequence (motif I) is the signature feature of the ligase/capping enzyme superfamily of nucleotidyl transferases that form a covalent lysyl-NMP intermediate (FIG. 4). The contributions of motif I residues Lys115 and Asp117 to the activity of AmEPV ligase were gauged from the effects of single alanine substitutions. Mutant proteins K115A and D117A were produced in bacteria and purified from soluble lysates by nickel-affinity and phosphocellulose chromatography (FIG. 5A). The K115A and D117A mutants were both inert in nick ligation (FIG. 5B). K115A was also inert in ligase-AMP formation with [$\alpha$-$^{32}$P]$NAD^+$ (FIG. 5C), consistent with Lys115 being the site of covalent AMP attachment. The D253A protein reacted weakly with $NAD^+$ to form trace amounts of the ligase-AMP intermediate (FIG. 5C). The essentiality of the motif I Lys and Asp positions for nick joining by AmEPV ligase is consistent with structure-function studies of other DNA ligases, including the $NAD^+$-dependent *Thermus thermophilus* and *E. coli* DNA ligases, the ATP-dependent Chlorella virus DNA ligase, and the ATP-dependent ligase of the archaeon *Methanobacterium thermoautotrophicum* (18–21).

EXAMPLE 3
Substrate Specificity of AmEPV Ligase

Figure 6:
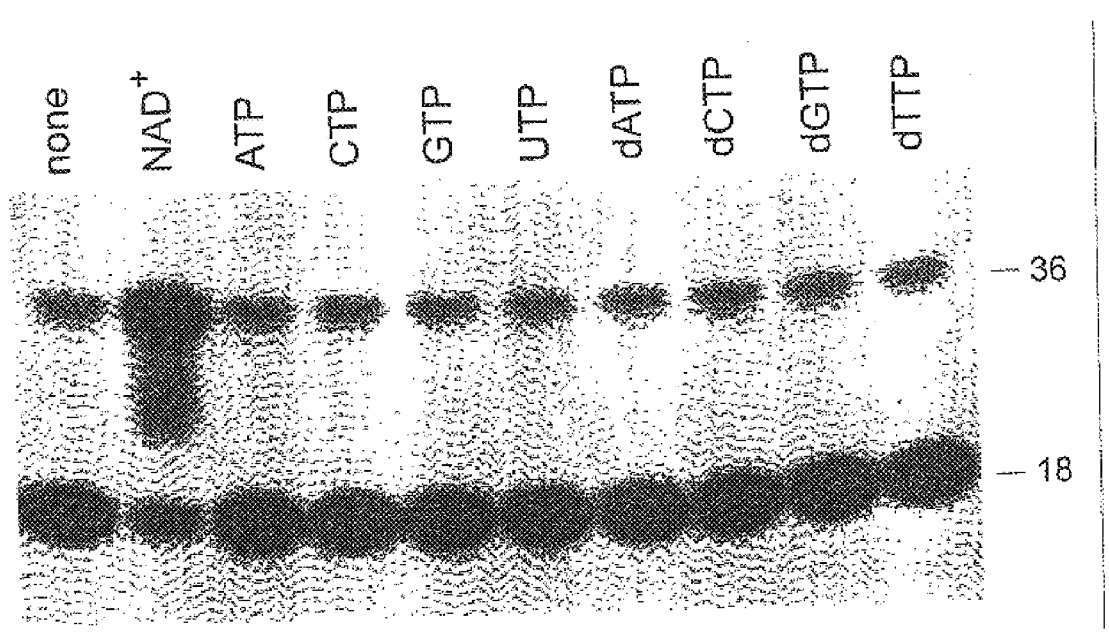
FIG. 6 shows the nucleotide cofactor specificity of AmEPV ligase. Reaction mixtures (20 μl) containing 50 mM Tris-HCl (pH 7.5), 10 mM (NH$_4$)$_2$SO$_4$, 5 mM DTT, 5 mM MgCl$_2$, 1 pmol of $^{32}$P-labeled nicked DNA, 32 ng of AmEPV ligase, and 50 μM of the indicated nucleotide were incubated for 30 min at 22° C. A control reaction contained no added nucleotide cofactor (none). The reaction products were resolved by polyacrylamide gel electrophoresis. An autoradiogram of the gel is shown.

A low level of nick ligation could be detected in the absence of added nucleotide (FIG. 6). Cofactor-independent ligation was attributed to pre-adenylated ligase in the enzyme preparation. The linear dependence of nucleotide-independent strand joining on input enzyme indicated that 15–20% of the enzyme molecules had AMP bound at the active site (not shown). Inclusion of $NAD^+$ in the reaction mixture stimulated nick ligation such that ~90% of the input substrate molecules were sealed (FIG. 6). Inclusion of ATP failed to stimulate the joining reaction above the level achieved in the absence of added nucleotide. Indeed, none of the standard rNTPs or dNTPs were able to satisfy the requirement of AmEPV ligase for a high energy cofactor (FIG. 6). NADP was also inactive (not shown). This experiment shows that the AmEPV enzyme is a bona fide $NAD^+$-specific DNA ligase, the first such enzyme identified from a eukaryotic source. Titration experiments showed that nick joining activity at sub-saturating levels of enzyme increased with $NAD^+$ concentration from 1 to 50 $\mu$M and plateaued at 50–100 $\mu$M (not shown). A $K_m$ of 9 $\mu$M $NAD^+$ was calculated from a double-reciprocal plot of the data.

Nick joining by AmEPV ligase required a divalent cation cofactor and was optimal at 5 mM magnesium. Manganese and cobalt (5 mM) were also active, albeit less than magnesium, whereas calcium, cooper, and zinc did not support ligase activity (not shown). The AmEPV ligase was active in Tris-HCl buffer from pH 6.5 to pH 9.0 (not shown).

EXAMPLE 4
Structure Probing of AmEPV Ligase By Limited Proteolysis

Figure 7:
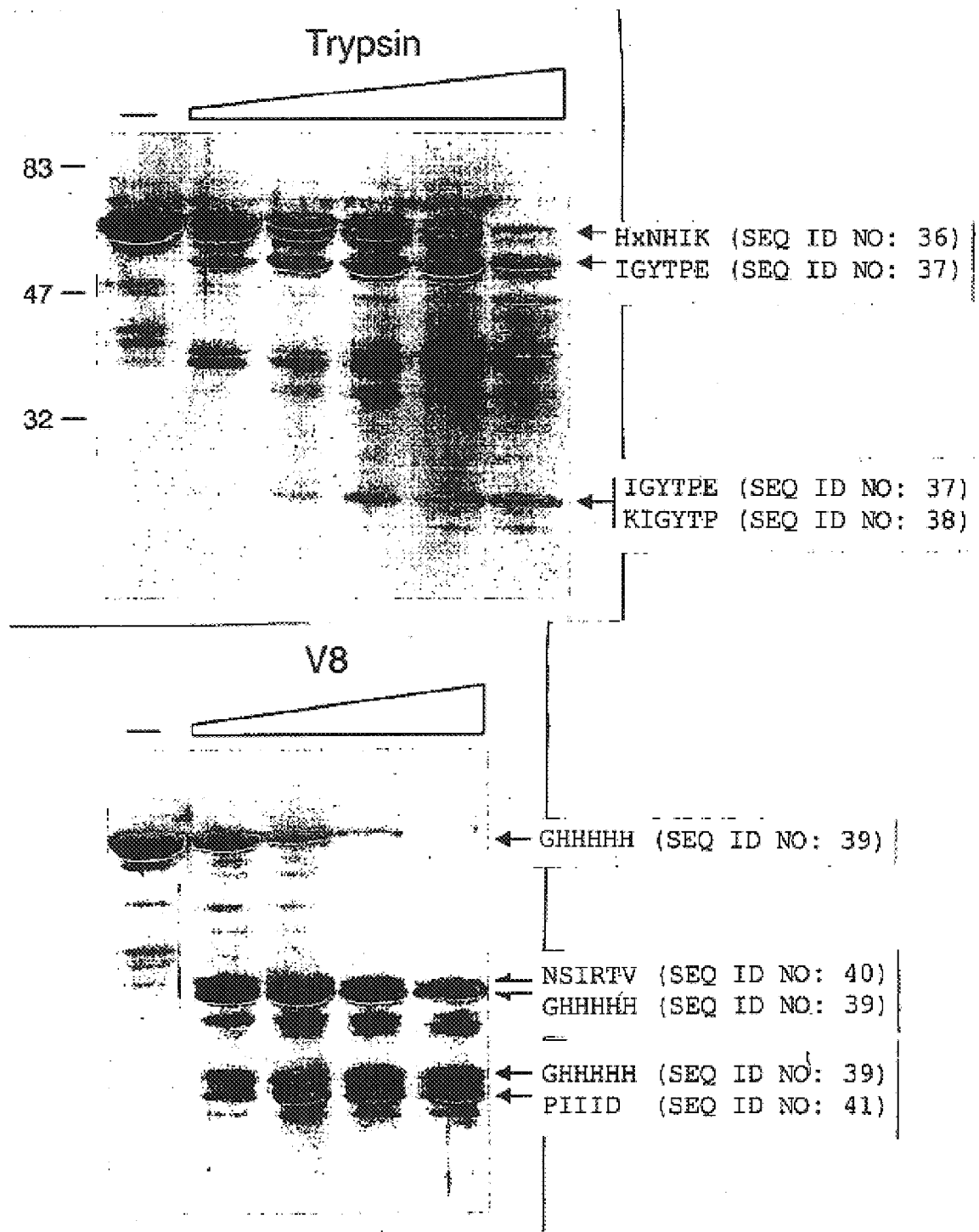
FIG. 7 shows the structural analysis of AmEPV DNA ligase by limited proteolysis. Proteolysis reaction mixtures (15 μl) containing 6 μg of AmEPV ligase and increasing amounts of trypsin (20, 40, 80, 160, or 320 ng) or V8 protease (62, 125, 250, or 500 ng) were incubated at 22° C. for 15 min. The samples were denatured in SDS and the proteolysis products were resolved by SDS-PAGE. A Coomassie-blue stained gel is shown. The positions and sizes (kDa) of marker proteins are indicated on the left.

Recombinant His-tagged AmEPV ligase was subjected to proteolysis with increasing amounts of trypsin and V8 proteases. N-terminal sequencing of the undigested AmEPV ligase polypeptide by automated Edman chemistry after transfer from an SDS-gel to a PVDF membrane confirmed that the N-terminal sequence (GHHHHH) (SEQ ID NO: 39) corresponded to that of the recombinant gene product starting from the second residue of the His-tag (FIG. 7). Apparently, the ligase suffered removal of the initiating methionine during expression in *E. coli*. Initial scission of the ligase by 20–40 ng of trypsin yielded two major products: (i) a~60 kDa species (sequence HxNHIK (SEQ ID NO: 36), where x is predicted to be M) resulting from tryptic cleavage of the His-tag 2 residues upstream of Met1 of the AmEPV protein, and (ii) a ~50 kDa species (sequence IGYTPE) (SEQ ID NO:37) resulting from cleavage between Lys70 and Ile71. The latter cleavage site, denoted by an arrow above the AmEPV sequence in FIG. 4, is conserved in other $NAD^+$ ligases and is located at the distal margin of a short $\alpha$ helix at the end of domain Ia in the crystal structures of Bst and Tfi ligases. It is surmised that the tryptic site demarcates a surface loop between domain Ia and the nucleotidyl transferase domain of AmEPV ligase. The 50 kDa proteolytic fragment became more abundant as trypsin was increased to 80 ng and it remained resistant to digestion by a concentration of trypsin in excess of that sufficient to cleave all the input ligase. A lower molecular weight product accumulated at higher trypsin concentrations; this species consisted of a mixture of two peptides with overlapping N-termini derived from scission at Lys70/Ile71 and Lys69/Lys70 (FIG. 7). This product apparently resulted from a discrete secondary cleavage within the nucleotidyl transferase/OB domain; however, the C-terminus of the tryptic product was not determined.

Treatment of AmEPV ligase with V8 protease yielded two clusters of products that were resistant to digestion by V8 concentrations sufficient to cleavage all of the input ligase (FIG. 7). The higher molecular weight cluster consisted of a major component that retained the original N-terminus of the His-tag (GHHHHH) (SEQ ID NO:39) and a minor species (sequence NSIRTV) (SEQ ID NO:40) arising from cleavage between Glu225 and Asn226 within the nucleotidyl transferase domain (see FIG. 4). The Glu/Asn site is conserved in Tfi ligase (as Glu246/Lys247), where it is exposed on the protein surface. The lower molecular weight cluster includes a fragment that retains the His-tag and a second species (sequence PIIID) generated by cleavage between Glu316 and Pro317 within the second $\beta$ strand of the OB-fold domain (See FIG. 4). The Glu/Pro V8 cleavage site is conserved in the other $NAD^+$ ligases and is exposed on the protein surface in the Tfi ligase crystal structure (15).

EXAMPLE 5
Characterization of N-terminal and C-terminal Domains of AmEPV Ligase The proteolysis results prompted the construction of the N-terminal deletion mutant Lig(71–532) and the C-terminal truncation Lig(1–316), referred to henceforth as NΔ70 and CΔ216, respectively. The NΔ70 protein corresponds to the major trypsin-resistant species and it lacks all of domain Ia. The CΔ216 protein is truncated at the V8-accessible site in the middle of the OB-fold and lacks all of the HhH domain. NΔ70 and CΔ216 were produced in bacteria as N-terminal $His_{10}$-fusions and purified from soluble lysates by Ni-agarose and phosphocellulose chromatography (FIG. 8A).

CΔ216 was incapable of sealing a 3'—OH/5'-$PO_4$ nick (FIG. 8C), yet it retained the ability to react with $NAD^+$ to form a covalent ligase-adenylate intermediate (FIG. 8B). It is surmised that the OB and/or HhH domains are critical for AmEPV ligase function at a step subsequent to step 1 reaction chemistry. These findings echo those of Timson and Wigley (22) for an N-terminal domain of Bst ligase that was truncated within the first β strand of the OB-fold domain but retained step 1 ligase-adenylation activity.

The fact that no accumulation of a DNA-adenylate intermediate could be detected during the reaction of CΔ216 with nicked DNA in the presence of $NAD^+$ hinted that the missing C-terminus played a role either in step 2 chemistry or in DNA binding. Conceivably, the C-terminus may also be required for step 3 of the ligase reaction, i.e. the formation of a phosphodiester bond.

Therefore, step 3 of the AmEPV ligation reaction was assayed using a pre-adenylated nicked DNA substrate. The adenylated strand used to form this substrate was synthesized by ligase-mediated AMP transfer to the 5' $^{32}$P-labeled strand of a DNA molecule containing a 1-nucleotide gap (8, 23). The radiolabeled AppDNA strand was purified by denaturing PAGE and then annealed to an unlabeled 36-mer template oligonucleotide and a 3' OH 18-mer oligonucleotide to form the nicked DNA-adenylate molecule illustrated in FIG. 8C. This substrate was reacted with excess wild-type or truncated AmEPV ligase in the presence of magnesium without added $NAD^+$. The wild type enzyme generated a 36-mer ligation product, but CΔ216 was inert in phosphodiester formation (FIG. 8C, AppDNA). Thus, the ligation defect incurred by the loss of the C-terminus could not be overcome by bypassing the DNA adenylation step.

A novel finding that emerged from the deletion analysis was that elimination of the N-terminal Ia domain abrogated nick joining by a completely different mechanism than did the loss of the C-terminus. NΔ70 was inert in the overall ligation reaction (FIG. 8C) and formation of a ligase-adenylate intermediate with $NAD^+$ (FIG. 8B). However, NΔ70 was fully functional in synthesis of phosphodiester bond at a pre-adenylated nick (FIG. 8C). The latter point underscores that the step 1 defect of NΔ70 cannot be ascribed to a global folding defect, but instead reflects a specific requirement for domain Ia in the reaction of ligase with $NAD^+$.

Several instructive points were gleaned from a kinetic analysis of phosphodiester bond formation by WT ligase and NΔ70 at a pre-adenylated nick under conditions of ligase excess (FIG. 9A). First, although the extent of sealing of the preadenylated nick in the absence of $NAD^+$ was identical for WT ligase and NΔ70, the rate of the NΔ70 was 50% faster than that of the WT enzyme. The implication of this result is that the presence of domain Ia constitutes a modest impediment to the interaction of the ligase with nicked DNA adenylate. Second, the inclusion of 50 μM $NAD^+$ elicited a 5-fold decrement in the extent of step 3 ligation by the wild-type ligase, presumably by competition of $NAD^+$ and nicked DNA adenylate for the AMP-binding pocket within the nucleotidyl transferase domain. $NAD^+$ had no effect whatsoever on step 3 catalysis by NΔ70, consistent with a critical role for domain Ia in $NAD^+$-binding to AmEPV ligase.

EXAMPLE 6
Binding of AmEPV Ligase to DNA-adenylate

A native gel mobility shift assay was used to directly examine the binding of AmEPV ligase to the nicked DNA-adenylate substrate. Phosphodiester formation on the nicked DNA-adenylate substrate required a divalent cation cofactor (not shown); therefore, the binding reactions were performed in the absence of a divalent cation so as to preclude conversion of substrate to product during the incubation. Mixing the WT ligase (2 pmol) with 200 fmol of nicked DNA-adenylate resulted in the formation of a discrete protein-DNA complex that migrated more slowly than the free AppDNA (FIG. 9B). Mixture with NΔ70 yielded a discrete complex that migrated just slightly faster than the WT ligase-DNA complex, consistent with loss of mass and/or charge with deletion of domain Ia. Doubling the amount of ligase to 4 pmol resulted in increased abundance of both the WT and NΔ70 complexes. From the amount of protein required to shift 50% of the DNA, it was estimated that the affinity of NΔ70 for nicked DNA-adenylate was ~100 nM. At 2 pmol of input ligase, NΔ70 appeared to have a slightly higher affinity for the AppDNA than WT ligase, which seconded the inference from the step 3 kinetic analysis (FIG. 9A) that the presence of domain Ia may impede AppDNA binding. The CΔ216 protein failed to bind AppDNA at all (FIG. 9B), suggesting that the lack of step 3 catalytic activity (FIG. 8C) can be ascribed to a primary DNA binding defect.

EXAMPLE 7
Single Mutations in Domain Ia of AmEPV Ligase Affect $NAD^+$ Binding and Nick Ligation To further probe the role of domain Ia in $NAD^+$ recognition and nucleotidyl transfer, single alanine substitutions were introduced at six positions in the Ia domain of AmEPV ligase. The six mutated residues—Asp27, Tyr39, Tyr40, Asp48, Tyr51, and Asp52—are conserved in the $NAD^+$-dependent Eco, Bst and Tfi DNA ligases and are denoted by ✓ in FIG. 4. The D27A, Y39A, Y40A, D48A, Y51A, and D52A proteins were produced in *E. coli* and purified by Ni-agarose and phosphocellulose column chromatography in parallel with WT ligase (FIG. 10A). Ligation of singly nicked 3'—OH/5'$PO_4$ DNA by WT ligase was proportional to input protein and attained saturation with ~90% of the input nicks converted to phosphodiesters (FIG. 10C). The specific activity of the D27A protein was equivalent to that of the WT ligase; however, the other alanine mutations elicited significant defects in nick joining (FIG. 10C). The specific activities of the mutants relative to WT ligase were as follows: Y39A (26%); Y40A (5%); D48A (6%); Y51A (<0.5%) and D52A (21%). The defects in nick sealing were accompanied by defects in the reactions of the mutants proteins with $NAD^+$ to form the covalent ligase-adenylate intermediate (FIG. 10D). In particular, the Y51A mutant was inert in both nick ligation and ligase adenylation. However, control experiments confirmed that Y51A and the four other defective Ia mutants Y39A, Y40A, D48A, and D52A were catalytically active in step 3 phosphodiester formation with the nicked DNA-adenylate substrate (not shown). Thus, specific functional groups within domain Ia are important for the reaction of ligase with NAD+ but are not required for catalysis when the AMP pocket of the nucleotidyl transferase domain is filled by the adenylated DNA intermediate. These results have important mechanistic implications that bear on issues of drug discovery.

EXAMPLE 8
Domain Ia of *E. coli* DNA Ligase (LigA) Is Required for Reaction With NAD+

The present discoveries concerning the role of domain Ia in adenylate transfer from NAD+ by the AmEPV ligase were extended to bacterial NAD+-dependent enzymes exemplified by the NAD+ ligase of *Escherichia coli*. Prior studies has shown that N-terminal deletions NΔ78 and NΔ38 of *E. coli* DNA ligase LigA, which eliminate all or part of domain Ia, result in complete loss of nick joining activity (19). To probe the essential role of domain Ia in the ligase reaction, the effects of the NΔ78 and NΔ38 mutations on individual steps in the reaction pathway were examined. The first step in DNA ligation involves formation of a covalent enzyme-adenylate intermediate. The purified recombinant wild-type Eco LigA and the NΔ78 and NΔ38 mutants are shown in FIG. 12A. Whereas incubation of wild-type EcoLigA with [$^{32}$P-AMP]NAD+ and magnesium resulted in the formation of a $^{32}$P-labeled covalent nucleotidyl-protein adduct that comigrated with the full-sized ligase polypeptide during SDS-PAGE, the NΔ78 and NΔ38 mutants were inert in ligase adenylation (FIG. 12B).

The third step of the ligation pathway entails attack of the 3' OH of the nick on the 5' PO$_4$ of the DNA-adenylate to form a phosphodiester and release AMP. Step 3 of the ligation reaction was assayed using a pre-adenylated nicked DNA substrate labeled with $^{32}$P on the 5' PO$_4$ of the DNA-adenylate strand (FIG. 13). Reaction of wild-type EcoLigA with the nicked DNA-adenylate in the presence of magnesium without added NAD+ resulted in strand closure, evinced by formation of a radiolabeled 36-mer product. NΔ78 and NΔ38 were also capable of forming a phosphodiester bond at the pre-adenylated nick (FIG. 13). The latter finding underscores that abrogation of the overall nick joining reaction by the NΔ78 and NΔ38 deletions cannot be ascribed to a global folding defect, but instead reflects a specific requirement for domain Ia in the reaction of *E. coli* ligase with NAD+.

EXAMPLE 9
Single Alanine Mutations in Domain Ia of *E. coli* DNA Ligase LigA Affect NAD+ Binding and Nick Ligation To further probe the role of domain Ia in NAD+ recognition and nucleotidyl transfer, single alanine substitutions were introduced at six positions in the Ia domain of *E. coli* LigA. The six mutated Eco ligase residues—Glu10, Tyr22, His23, Asp32, Tyr35, and Asp36—correspond to the six residues that were subjected to alanine scanning mutagenesis in AmEPV ligase (FIG. 11). Five of the six positions (Tyr22, His23, Asp32, Tyr35, and Asp36) are conserved in the NAD+-dependent ligases from 27 different bacterial species (FIG. 11). The conserved positions are denoted by shaded boxes in FIG. 11. The Eco ligase mutants E10A, Y22A, H23A, D32A, Y35A, and D36A were produced in *E. coli* and purified by Ni-agarose chromatography in parallel with wild-type ligase (FIG. 12A). The extent of ligation of singly nicked 3'—OH/5'PO$_4$ DNA by wild-type Eco LigA was proportional to input protein, and ~80% of the input nicked substrate was sealed at saturating levels of enzymes (FIG. 12C). The specific activity of the E10A protein was 90% that of the wild-type ligase; however, the other alanine mutations elicited significant defects in nick joining (FIG. 12C). The specific activities of the mutants relative to wild-type ligase were as follows: Y22A (0.1%); H23A (10%); D32A (0.2%); Y35A (2%) and D36A (0.2%) (Table 1). The defects in nick sealing were accompanied by defects in the reactions of the mutant proteins with NAD+ to form the covalent ligase-adenylate intermediate (FIG. 12B). In particular, the Y22A, D32A, and D36A mutants were virtually inert in both nick ligation and ligase adenylation. H23A and Y35A, which were less active than wild-type ligase in nick joining, were also less active in ligase-AMP formation. The E10A mutation, which had no effect on nick joining, also did not affect the yield of ligase-AMP adduct (FIG. 2B and data not shown).

Figure 14A:
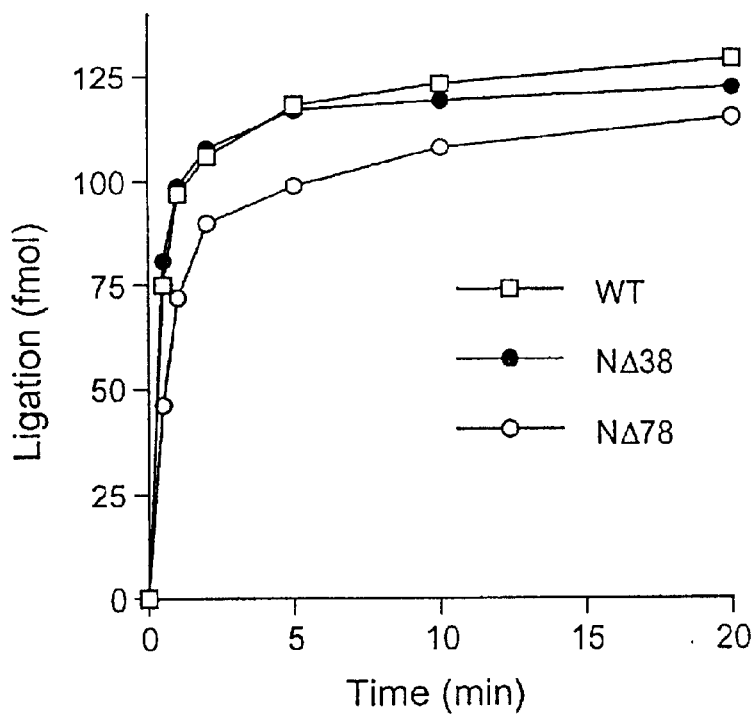
Figure 14B:
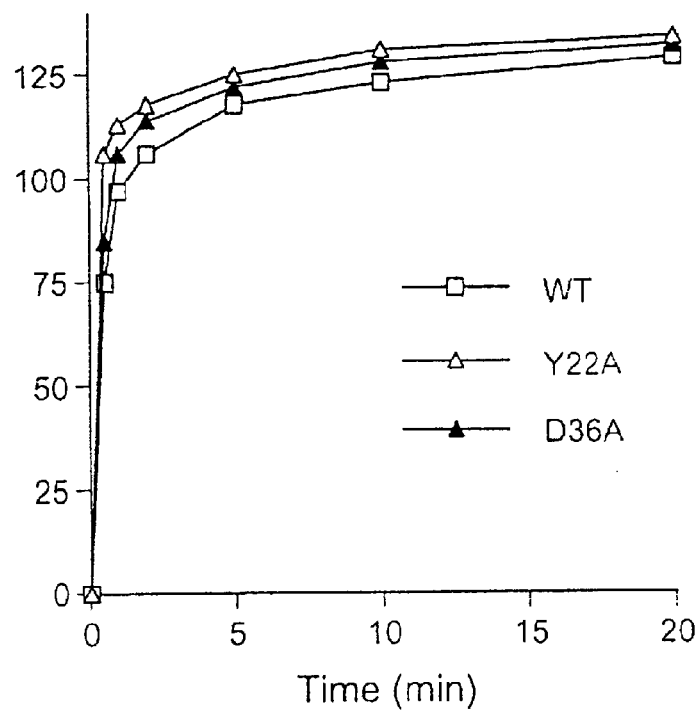

Control experiments confirmed that all of the domain Ia mutants (E10A, Y22A, H23A, D32A, Y35A, and D36A) were catalytically active in phosphodiester formation with nicked DNA-adenylate substrate (FIG. 13). A kinetic analysis of the sealing of nicked DNA-adenylate by wild-type ligase, the domain Ia deletion mutants, and two of the Ala-mutants is presented in FIG. 14. The Y22A and D36A mutations, which suppressed the catalysis of nick joining and ligase adenylation, had no effect on the rate or the extent of phosphodiester formation at a pre-adenylated nick (FIG. 14B). A deletion of the N-terminal 38-amino acids of domain Ia also had no effect on the rate or yield of the isolated step 3 reaction and the more extensive NΔ78 deletion had only a modest (2-fold) effect on the rate of approach to the endpoint (FIG. 14A). These experiments show that specific functional groups within domain Ia of *E. coli* LigA are important for the reaction of ligase with NAD+ but are not required for catalysis when the AMP pocket of the nucleotidyl transferase domain is filled by the adenylated DNA intermediate

EXAMPLE 10
Effects of Conservative Mutations in Domain Ia of *E. coli* LigA

To evaluate the roles of charge, hydrogen bonding potential, and steric constraints in the functions of the domain Ia residues implicated in the step 1 reaction with NAD+, the effects of conservative substitutions were tested. Tyr22 and Tyr35 were replaced by Phe and Ser, His23 was changed to Tyr, and Asp32 and Asp36 were mutated to Glu and Asn. The recombinant mutant ligases were purified from soluble bacterial extracts by Ni-agarose chromatography (FIG. 15A). The specific activity of each mutant was determined under steady-state conditions by protein titration and normalized to the specific activity of wild-type ligase. The results are summarized in Table 1. The salient findings were that the Y22F and Y35F changes partially restored ligase activity (to 9% and 23% of wild-type, respectively), whereas serine substitutions had no salutary effect. It is concluded that aromatic groups at positions 22 and 35 are important for strand joining and that activity is optimal when tyrosine is present. All NAD+-dependent ligases have a tyrosine at the position equivalent to Tyr22 of EcoLigA; position 35 is predominantly tyrosine and rarely phenylalanine in other NAD+-dependent enzymes (FIG. 11). Replacing His23 of EcoLigA by tyrosine restored activity to near-wild type level (88%). Most NAD+-dependent ligases naturally contain tyrosine at this position and only a minority of the bacterial enzymes have histidine in its place (FIG. 11). Introduction of asparagine in place of Asp32 or Asp36 partially restored ligase activity to 9% and 12% of the wild-type level, respectively. This represents a significant gain of function compared to the D32A and D36A mutants (0.2% activity). Changing aspartate to glutamate was of no benefit at position 32 and conferred a lesser restoration of function at position 36 than did asparagine (Table 1). Thus, whereas aspartates at positions 32 and 36 confer optimal strand joining activity, the isosteric amide functional groups are tolerated with a significant, but not catastrophic, activity decrement. It is inferred that hydrogen-bonding interactions of the Asp32 and Asp36 functional groups are critical for activity and that the ligase does not tolerate lengthening of the distance from the main chain to the carboxylates, presumably because of steric clashes. Positions 32 and 36 are strictly conserved as aspartate in all NAD$^+$-dependent ligases (FIG. 11).

TABLE 1

Effects of Domain Ia Mutations on the Nick Joining Activity of *E. coli* LigA

| LigA Mutant | Nick Joining Activity (% of WT) |
|---|---|
| E10A | 90 |
| Y22A | 0.1 |
| Y22F | 9 |
| Y22S | 0.2 |
| H23A | 10 |
| H23Y | 88 |
| D32A | 0.2 |
| D32E | 0.4 |
| D32N | 9 |
| Y35A | 2 |
| Y35F | 23 |
| Y35S | <0.1 |
| D36A | 0.2 |
| D36E | 4 |
| D36N | 12 |

EXAMPLE 11

Effects of Conservative Domain Ia Mutations on Ligase-AMP Formation

The effects of the conservative domain Ia mutations on the reactions of the recombinant ligases with NAD$^+$ to form covalent ligase-adenylate intermediate paralleled the effects on the composite nick joining reaction (FIG. 15B). The Y22F mutant was weakly active in ligase adenylation, whereas the Y22S protein was virtually inert. Y35F restored adenylation activity, but the Y35S mutant was apparently unreactive with NAD$^+$. The H23Y change restored the yield of ligase-AMP adduct to the wild-type level. The D32N and D36N proteins were partially active, while the D32E and D36E ligases were more severely affected.

Figure 16A:
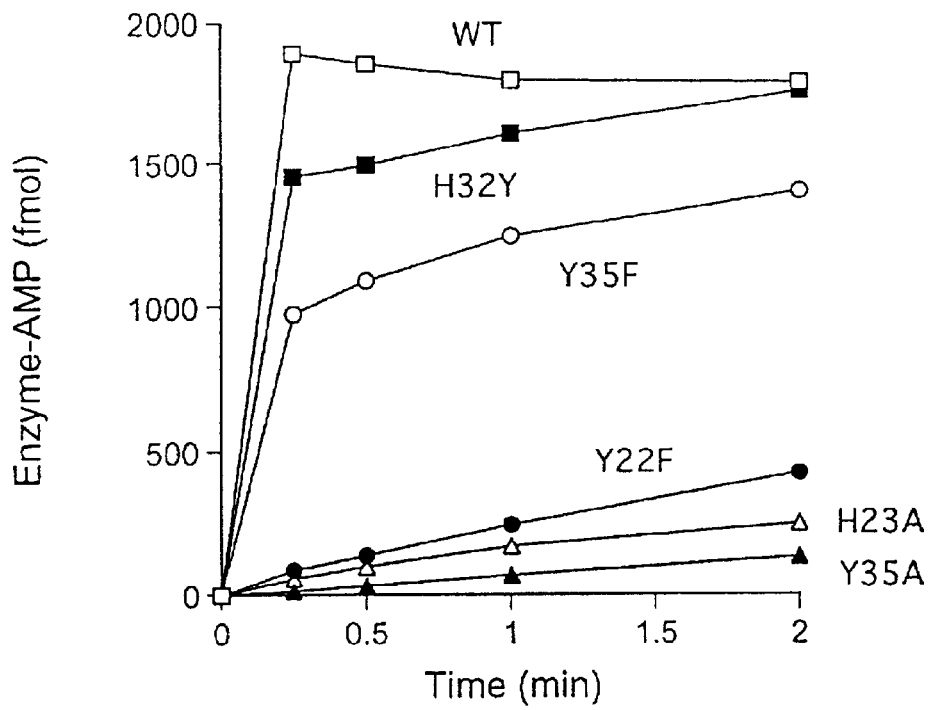
Figure 16B:
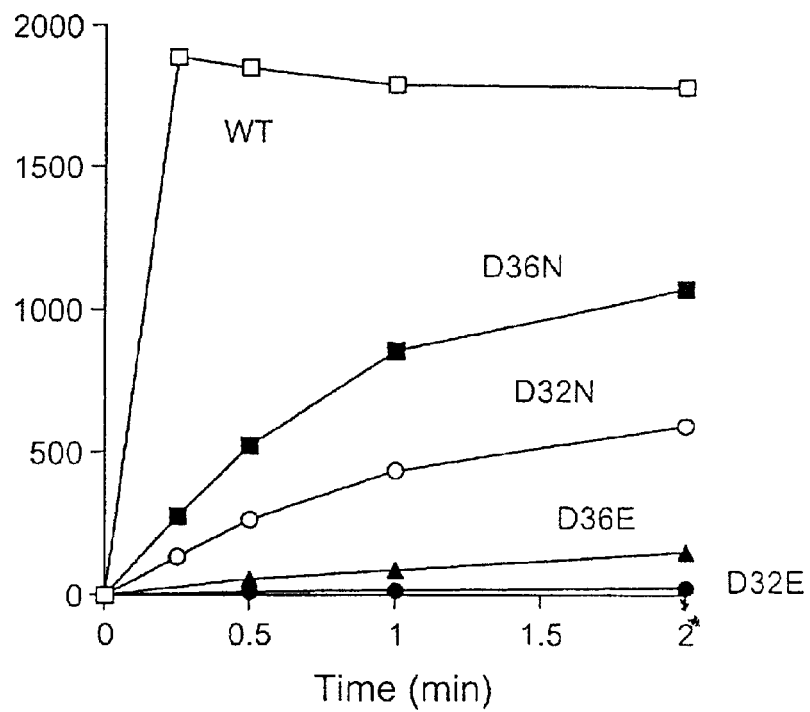

A kinetic analysis of the reaction of EcoLigA with 1 μM [$^{32}$P-AMP]NAD$^+$ is shown in FIG. 16. Wild-type ligase attained its reaction endpoint in ≦15 s (the earliest time tested) with ~24% of the input ligase molecules being labeled with $^{32}$P-AMP. Mutational effects on the rates of ligase adenylation were generally consistent with the hierarchy of effects on the steady-state nick joining reaction. H23Y, which had the highest nick joining activity (88%) of the conservative domain Ia mutants, displayed a kinetic pattern similar to wild-type ligase, whereas catalytically impaired mutants H23A and Y22F (9–10% activity) reacted slowly (FIG. 16A). Y35F was adenylated faster than Y35A (FIG. 16A); D32N was faster than D32E and D36N was faster than D36E (FIG. 16B). These results indicate that the conserved Tyr22, His23, Asp32, Tyr35, and Asp36 side chains are constituents of the NAD$^+$ binding site of bacterial DNA ligase.

EXAMPLE 12

Mechanistic Implications

Figure 17A:
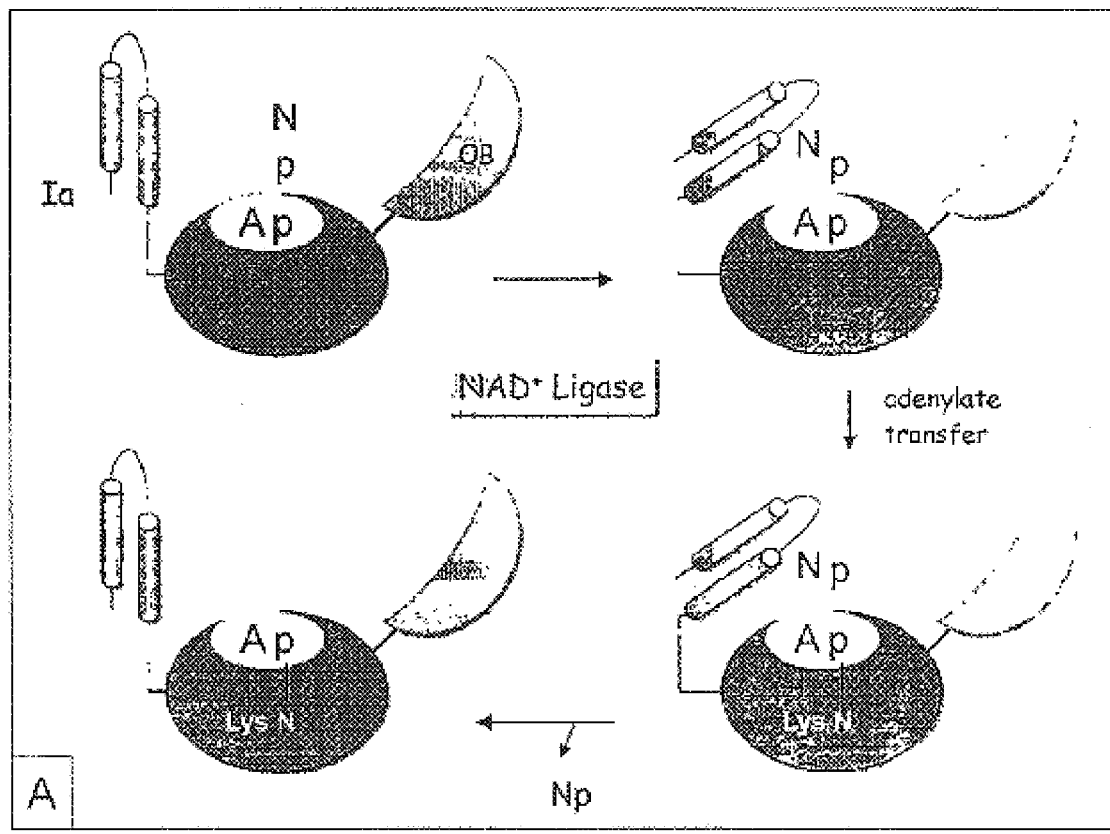

The selective effects of deletions and mutations in domain Ia of AmEPV ligase and Eco ligase on nucleotidyl transferase reaction with NAD$^+$ provide the first evidence for a common structural determinant of substrate specificity for the NAD$^+$ ligase family. Domain Ia consists principally of two antiparallel α helices and an intervening loop (FIG. 17A). Domain Ia is unique to NAD$^+$-dependent ligases and there is no discernable counterpart in any member of the ATP-dependent ligase family; thus, it is sensible that domain Ia is involved in NAD$^+$ recognition.

Figure 17B:
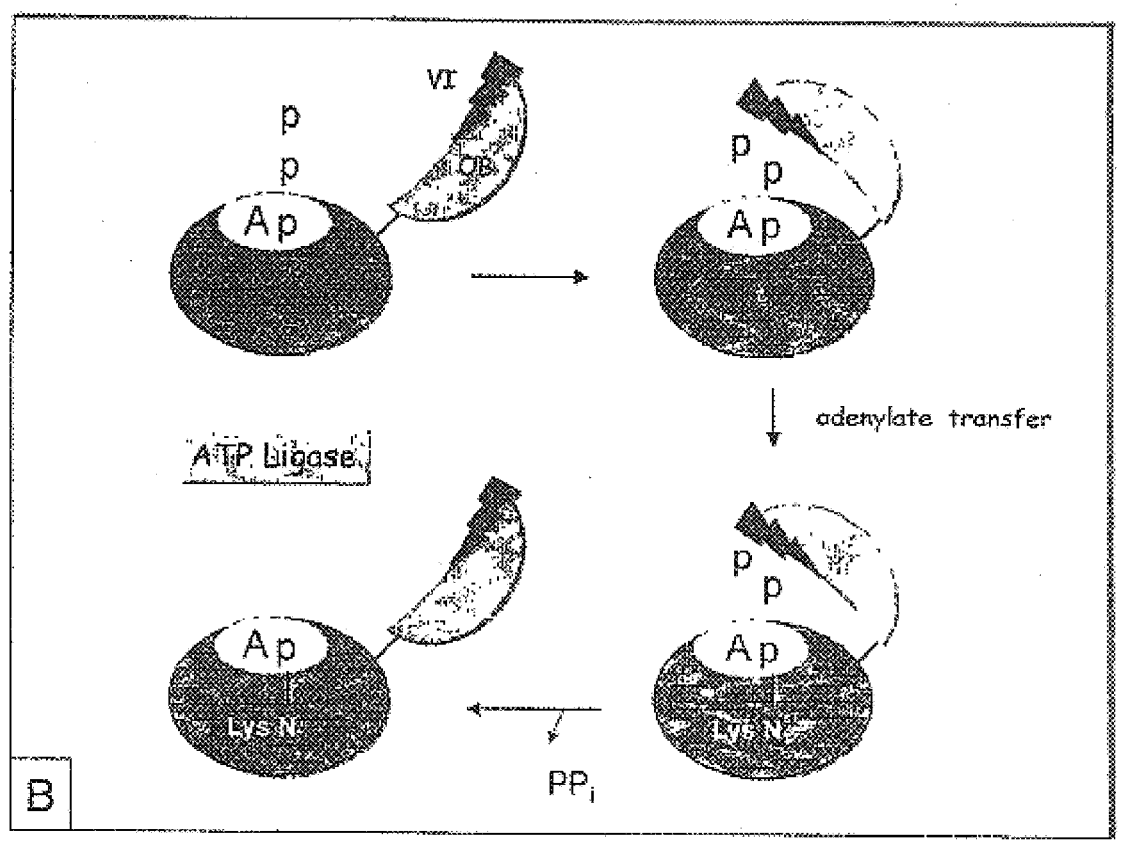

The results suggest a mechanistic model whereby ligase substrate specificity at the step of ligase-adenylate formation is determined for the NAD$^+$-dependent enzymes by the interactions of domain Ia with the NMN moiety of NAD$^+$ (FIG. 17A). For the ATP-dependent ligases, it is determined by the interactions of motif VI of the OB-fold domain with the β and γ phosphates of ATP (FIG. 17B). The crystal structures of NAD$^+$ ligase, ATP ligases, and mRNA capping enzyme in various functional states all indicate that contacts of the enzymes with the AMP or GMP moieties are confined to the nucleotidyl transferase domain (2, 3, 7, 15). The nucleoside portion is buried within a pocket while the α phosphate is exposed on the surface of the domain. The first step in ligation and capping entails in-line attack of the motif I lysine on the nucleoside triphosphate or NAD$^+$ substrates to form enzyme-adenylate or enzyme-guanylate. The reaction is believed to proceed through a pentacoordinate phosphorane transition state in which the attacking lysine nucleophile is apical to the pyrophosphate or NMN leaving group. The ground state structures of T7 ligase with ATP and capping enzyme with GTP reveal that the pyrophosphate leaving group projects out into the open cleft between the nucleotidyl transferase and OB-fold domains and that it makes few or no direct contacts with the enzyme. Indeed, the β and γ phosphates in the ground state are oriented unfavorably with respect to the motif I lysine so that reaction chemistry is effectively precluded.

The catalysis of nucleotidyl transfer by ATP ligase and capping enzyme is believed to be facilitated by closure of the OB-fold domain over the nucleotide binding pocket such that motif VI (located at the C-terminus of the OB-fold) makes direct contact with the β and γ phosphates and reorients the pyrophosphate leaving group so that it is apical to the attacking lysine (3, 7). The conformational switch is illustrated for ATP ligase in FIG. 17B. Once the proper orientation is attained, the lysyl-N-AMP intermediate is formed and pyrophosphate is expelled. The breaking of the α-β phosphoanhydride bond releases the tether of motif VI to the nucleotidyl transferase domain and triggers the adoption of a wide open domain conformation that permits the binding of nicked DNA substrate immediately above the AMP phosphate on the surface of the nucleotidyl transferase domain (3). Motif VI, though essential for ligase-AMP formation, is dispensable for step 3 phosphodiester formation (8).

There is no equivalent of motif VI in the OB-fold of the NAD$^+$ ligases; this is sensible insofar as they have no need for contacts with a γ phosphate. Yet, ligase-adenylate formation by the NAD$^+$ ligases should still require an apical orientation of the nicotinamide nucleotide phosphate moiety of NAD$^+$ with respect to the motif I lysine nucleophile. The results presented herein suggest that the proper orientation of NAD$^+$ is achieved by closure of domain Ia over the nucleotide binding pocket, resulting in contacts between domain Ia and the nicotinamide nucleoside (and perhaps also the phosphate of the leaving group). The breaking of the α-β phosphoanhydride bond of NAD$^+$ upon enzyme-adenylate formation would release the tether of domain Ia to the nucleotidyl transferase domain and allow domain Ia to spring apart to adopt the conformation observed in the crystal structure of the Tfi ligase-adenylate intermediate (15).

There is as yet no published crystal structure of an NAD$^+$ ligase bound to NAD$^+$. However, the analysis of the effects of single alanine mutations in domain Ia of AmEPV and Eco DNA ligases identifies five residues (Y22A, H23A, D32A, Y35A, and D36A in Eco LigA) that are involved specifically in adenylate transfer from $NAD^+$. These five residues are conserved in the $NAD^+$ ligases from 27 other bacterial species (shown in FIG. 11) and in many other bacterial $NAD^+$ ligases that are not shown. Indeed, the five side chains are tightly clustered on the same surface of domain Ia in the Tfi ligase crystal structure. Accordingly, it is likely that these residues are constituents of an NMN binding site. The AmEPV ligase residue Asp27 and the Eco ligase residue Glu10, which occupy equivalent positions in domain Ia, are not important for ligase function, i.e., alanine substitutions are benign in both ligases. Although the corresponding position is conserved as a carboxylate in the Bst and Tfi ligases, it is not conserved in numerous other bacterial $NAD^+$ ligases (FIG. 11).

The structures of domain Ia of Tfi and Bst ligases consist principally of two antiparallel α helices and an intervening loop (FIG. 17A). In the Tfi and Bst ligases, the essential aspartates (Asp34 and Asp38, corresponding to EcoLigA residues Asp32 an Asp36) are located on the enzyme surface with their Oδ atoms separated by 3.5–5.6 Å. This pair of surface Asp residues may coordinate the vicinal ribose oxygens of the nicotinamide nucleoside via hydrogen bonding. Alternatively, the aspartates may interact with the nicotinamide base. A role for the surface aspartates in coordinating a divalent cation seems less attractive, insofar as their replacement by asparagine results in partial recovery of activity, but glutamate substitutions are ineffective. Tyr24 in Tfi and Bst ligases (corresponding to essential Tyr22 in EcoLigA) is positioned with its phenolic hydroxyl 3.2–4.0 Å from Oδ of Asp34 (essential Asp32 in EcoLigA). The Asp-Tyr contact may be functionally important, insofar as the Tyr is invariant and its replacement by Phe results in an order of magnitude decrement in ligase activity. Loss of the aromatic ring of Tyr22 in EcoLigA abolishes ligase function, which could reflect an interaction of the tyrosine with the nicotinamide ring. Tyr25 of Tfi and Bst ligases (His23 in EcoLigA) is located on the enzyme surface and its phenolic hydroxyl is not within hydrogen-bonding distance of other constituents of the protein. The tyrosine/histidine side chain may interact via a hydrogen bond with $NAD^+$.

EXAMPLE 13
Implications for Ligase Pharmacology

Inhibitors of bacterial $NAD^+$-dependent DNA ligases are outstanding candidates for effective broad spectrum antibiotic therapy, because: (i) $NAD^+$-dependent ligases are present in all bacteria and are essential for bacterial growth in each case that has been studied; (ii) they are structurally conserved among bacteria, but display unique substrate specificity compared to the ATP-dependent ligases of humans and other mammals; and (iii) humans have no ortholog of an $NAD^+$ ligase. Arguably, the attractiveness of $NAD^+$ ligases as targets for drug discovery was tempered by the crystallographic evidence that the tertiary structure of the core nucleotidyl transferase and OB domains of $NAD^+$ ligases, as well as the active site pocket within the nucleotidyl transferase domain, are strikingly similar to those of ATP ligases despite scant similarity in their respective amino acid sequences.

The present discoveries concerning the function of domain Ia in $NAD^+$ ligase raise the prospects for identifying small molecules that either compete for the predicted NMN site on domain Ia (said site being absent from ATP ligases) or else interfere with the conformational movements of domain Ia that are postulated to orchestrate the adenylate transfer reaction from $NAD^+$ (FIG. 17). Inspection of Tfi ligase structure suggests that the domain closure step could occur by flexion of the loop that connects Ia to the nucleotidyl transferase domain without invoking a significant rearrangement within Ia. Thus, it would be fruitful to screen for candidate ligands that bind to the conserved and functionally important surface of domain Ia, using mutated domain Ia that are defective in the adenylation reaction as specificity controls.

The following references were cited herein:

1. Doherty and Suh. (2000) Nucleic Acids Res. 28, 4051–4058.
2. Subramanya et al. (1996) Cell 85, 607–615.
3. Odell et al. (2000) Molecular Cell 6, 1183–1193.
4. Shuman and Schwer. (1995) Mol. Microbiol. 17, 405–410.
5. Tomkinson et al. (1991) Proc. Natl. Acad. Sci. U.S.A. 88, 400–404.
6. Shuman and Ru. (1995) Virology 211, 73–83.
7. Håkansson et al. (1997) Cell 89, 545–553.
8. Sriskanda and Shuman. (1998) Nucleic Acids Res. 26, 4618–4625.
9. Konrad et al. (1973) J. Mol. Biol. 77, 519–529.
10. Gottesman et al. (1973) J. Mol. Biol. 77, 531–547.
11. Park et al. (1989) J. Bacteriol. 171, 2173–2180.
12. Petit and Ehrlich. (2000) Nucleic Acids Res. 28, 4642–4648.
13. Kaczmarek et al. (2001) J Bacteriol. 183, 3016–3024.
14. Singleton et al. (1999) Structure 7, 35–42.
15. Lee et al. (2000) EMBO J. 19, 1119–1129.
16. Afonso et al. (1999) J. Virol. 73, 533–552.
17. Bawden et al. (2000) Virology 274, 120–139.
18. Luo and Barany. (1996) Nucleic Acids Res. 24, 3079–3085.
19. Sriskanda et al. (1999) Nucleic Acids Res. 27, 3953–3963.
20. Sriskanda and Shuman. (1998) Nucleic Acids Res. 26, 525–531.
21. Sriskanda et al. (2000) Nucleic Acids Res. 28, 2221–2228.
22. Timson and Wigley. (1999) J. Mol. Biol. 285, 73–83.
23. Sekiguchi and Shuman. (1997) J. Virol. 71, 9679–9684.
24. Kerr et al. (1991) EMBO J. 10, 4343–4350.
25. Parks et al. (1998) Virus Res. 56, 135–147.
26. Chen et al. (1995) Mol Cell. Biol. 15, 5412–5422.
27. Wei et al. (1995) Mol. Cell. Biol. 15, 3206–3216.
28. Sekiguchi and Shuman. (1997) Nucleic Acids Res. 25, 727–734.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated $NAD^+$-dependant DNA ligase enzyme that is defective in its reaction with $NAD^+$ but is active in the ligation of pre-adenylated DNA nicks, wherein said DNA ligase is the *Amsacta moorei* entomopoxvirus $NAD^+$-dependent DNA ligase, wherein said DNA ligase is mutated by substituting one or more conserved residues selected from the group consisting of Tyrosine-39, Tyrosine-40, Aspartate-48, Tyrosine-51 and Aspartate-52 in domain Ia of the said DNA ligase wherein said conserved residues correspond to amino acid positions 21, 22, 30, 33 and 34 of SEQ. ID. NO: 1, respectively.

2. An isolated $NAD^+$-dependant DNA ligase enzyme that is defective in its reaction with $NAD^+$ but is active in the ligation of pre-adenylated DNA nicks, wherein said DNA ligase is the *Escherichia coli* $NAD^+$-dependent DNA ligase, wherein said DNA ligase is mutated by substituting one or more conserved residues selected from the group consisting of Tyrosine-22, Histidine-23, Aspartate-32, Tyrosine-35 and Aspartate-36 in domain Ia of the said DNA ligase wherein said conserved residues correspond to amino acid positions 21, 22, 31, 34 and 35 of SEQ. ID. NO: 2, respectively.

* * * * *

SEQUENCE LISTING

<160> NUMBER OF SEQ ID NOS: 41

<210> SEQ ID NO 1
<211> LENGTH: 377
<212> TYPE: PRT
<213> ORGANISM: Amsacta moorei entomopoxvirus
<220> FEATURE:
<221> NAME/KEY: CHAIN
<222> LOCATION: 19..395
<223> OTHER INFORMATION: NAD+-dependent DNA ligase

<400> SEQUENCE: 1

```
Tyr Ile Asp Ala Leu Asn Tyr Asn Asp Leu Glu Asn Ile Ile Gln
                 5                  10                  15

Thr Leu Asp Asn Ser Tyr Tyr Asp Lys Glu Ala Leu Ile Ser Asp
                20                  25                  30

Lys Lys Tyr Asp Leu Ile Arg Asn Phe Ile Asn Asn Lys Tyr Pro
                35                  40                  45

Asn Glu Ser Leu Cys Lys Lys Ile Gly Tyr Thr Pro Glu Asp Lys
                50                  55                  60

Val Arg Leu Lys Tyr Phe Met Gly Ser Glu Asn Lys Thr Tyr Lys
                65                  70                  75

Ser Asp Asn Lys Leu Leu Ser Trp Ile Asn Glu Tyr His Thr Asn
                80                  85                  90

Ile Leu Val Leu Ser Ala Lys Ala Asp Gly Ile Ser Val Leu Trp
                95                 100                 105

Asp Ile Lys Asn Asn Lys Ile Tyr Ser Arg Gly Asp Gly Lys Tyr
               110                 115                 120

Gly Lys Asp Ile Thr His Phe Ile Asn Tyr Phe Asn Phe Ser Asp
               125                 130                 135

Asp Lys Asn Ile Asn Asn Asp Ile Phe Lys Asn Asn Ile Asn
               140                 145                 150

Phe Val Arg Gly Glu Leu Val Ile Asp Lys Pro Glu Asn Arg Asn
               155                 160                 165

Ile Val Ala Gly Gln Ile Asn Arg Asn Glu Ile Asp Lys Glu Thr
               170                 175                 180

Ala Leu Lys Ile Tyr Phe Val Ala Tyr Glu Ile Leu Glu Pro Arg
               185                 190                 195

Met Thr Gln Leu Glu Gln Phe His Lys Leu Thr Glu Asn Ser Ile
               200                 205                 210

Arg Thr Val Lys Tyr Asp Ser Val Asp Tyr Asn Ile Ser Tyr Glu
               215                 220                 225

Gln Leu Ser Glu Ile Tyr Asn Asn Tyr Thr Gln Glu Leu Ser Tyr
               230                 235                 240

Tyr Ile Asp Gly Ile Ile Arg Asn Asn Leu Asn Pro Val
               245                 250                 255

Ile Lys Ser Gly Asn Pro Pro Trp Ser Ile Cys Phe Lys Glu Thr
               260                 265                 270

Asp Lys Ile Tyr Ile Thr Thr Val Lys Glu Ile Lys Trp Asp Ile
               275                 280                 285

Ser Lys Lys Asn Ile Tyr Ile Pro Lys Ala Ile Leu Glu Pro Ile
               290                 295                 300

Ile Ile Asp Asn Ser Thr Ile Asn Ala Val Ala Cys His Asn Ala
               305                 310                 315
```

-continued

```
Lys Tyr Val Ile Asp Lys Lys Ile Asn Thr Gly Ser Ile Val Glu
                320                 325                 330

Ile Val Lys Lys Gly Gly Val Ile Pro Ile Ile Asn Asn Val Ile
                335                 340                 345

Lys Glu Ser Asp Ile Glu Ile Ile Leu Pro Asp Gly Ile Leu Ser
                350                 355                 360

Gly Val Asn Ile Ile Phe Thr Gly Val Asn Lys Glu Ser Glu Ile
                365                 370                 375

Lys Arg

<210> SEQ ID NO 2
<211> LENGTH: 435
<212> TYPE: PRT
<213> ORGANISM: E. coli
<220> FEATURE:
<221> NAME/KEY: CHAIN
<223> OTHER INFORMATION: N-terminal portion of NAD+-dependent DNA ligase

<400> SEQUENCE: 2

Glu Ser Ile Glu Gln Gln Leu Thr Glu Leu Arg Thr Thr Leu Arg
                  5                  10                  15

His His Glu Tyr Leu Tyr His Val Met Asp Ala Pro Glu Ile Pro
                 20                  25                  30

Asp Ala Glu Tyr Asp Arg Leu Met Arg Glu Leu Arg Glu Leu Glu
                 35                  40                  45

Thr Lys His Pro Glu Leu Ile Thr Pro Asp Ser Pro Thr Gln Arg
                 50                  55                  60

Val Gly Ala Ala Pro Leu Ala Arg Phe Ser Gln Ile Arg His Glu
                 65                  70                  75

Val Pro Met Leu Ser Leu Asp Asn Val Phe Asp Glu Glu Ser Phe
                 80                  85                  90

Leu Ala Phe Asn Lys Arg Val Gln Asp Arg Leu Lys Asn Asn Glu
                 95                 100                 105

Lys Val Thr Trp Cys Cys Glu Leu Lys Leu Asp Gly Leu Ala Val
                110                 115                 120

Ser Ile Leu Tyr Glu Asn Gly Val Leu Val Ser Ala Ala Thr Arg
                125                 130                 135

Gly Asp Gly Thr Thr Gly Glu Asp Ile Thr Ser Asn Val Arg Thr
                140                 145                 150

Ile Arg Ala Ile Pro Leu Lys Leu His Gly Glu Asn Ile Pro Ala
                155                 160                 165

Arg Leu Glu Val Arg Gly Glu Val Phe Leu Pro Gln Ala Gly Phe
                170                 175                 180

Glu Lys Ile Asn Glu Asp Ala Arg Arg Thr Gly Gly Lys Val Phe
                185                 190                 195

Ala Asn Pro Arg Asn Ala Ala Gly Ser Leu Arg Gln Leu Asp
                200                 205                 210

Pro Arg Ile Thr Ala Lys Arg Pro Leu Thr Phe Phe Cys Tyr Gly
                215                 220                 225

Val Gly Val Leu Glu Gly Gly Glu Leu Pro Asp Thr His Leu Gly
                230                 235                 240

Arg Leu Leu Gln Phe Lys Lys Trp Gly Leu Pro Val Ser Asp Arg
                245                 250                 255

Val Thr Leu Cys Glu Ser Ala Glu Glu Val Leu Ala Phe Tyr His
                260                 265                 270
```

-continued

Lys Val Glu Glu Asp Arg Pro Thr Leu Gly Phe Asp Ile Asp Gly
            275                 280                 285

Val Val Ile Lys Val Asn Ser Leu Ala Gln Gln Glu Gln Leu Gly
            290                 295                 300

Phe Val Ala Arg Ala Pro Arg Trp Ala Val Ala Phe Lys Phe Pro
            305                 310                 315

Ala Gln Glu Gln Met Thr Phe Val Arg Asp Val Glu Phe Gln Val
            320                 325                 330

Gly Arg Thr Gly Ala Ile Thr Pro Val Ala Arg Leu Glu Pro Val
            335                 340                 345

His Val Ala Gly Val Leu Val Ser Asn Ala Thr Leu His Asn Ala
            350                 355                 360

Asp Glu Ile Glu Arg Leu Gly Leu Arg Ile Gly Asp Lys Val Val
            365                 370                 375

Ile Arg Arg Ala Gly Asp Val Ile Pro Gln Val Val Asn Val Val
            380                 385                 390

Leu Ser Glu Arg Pro Glu Asp Thr Arg Glu Val Val Phe Pro Thr
            395                 400                 405

His Cys Pro Val Cys Gly Ser Asp Val Glu Arg Val Glu Gly Glu
            410                 415                 420

Ala Val Ala Arg Cys Thr Gly Gly Leu Ile Cys Gly Ala Gln Arg
            425                 430                 435

<210> SEQ ID NO 3
<211> LENGTH: 427
<212> TYPE: PRT
<213> ORGANISM: Bacillus stearothermophilus
<220> FEATURE:
<221> NAME/KEY: CHAIN
<223> OTHER INFORMATION: N-terminal portion of NAD+-dependent DNA ligase

<400> SEQUENCE: 3

Gln Gln Ala Glu Arg Ala Ala Glu Leu Arg Glu Leu Leu Asn
            5                   10                  15

Arg Tyr Gly Tyr Glu Tyr Tyr Val Leu Asp Arg Pro Ser Val Pro
            20                  25                  30

Asp Ala Glu Tyr Asp Arg Leu Met Gln Glu Leu Ile Ala Ile Glu
            35                  40                  45

Glu Gln Tyr Pro Glu Leu Lys Thr Ser Asp Ser Pro Thr Gln Arg
            50                  55                  60

Ile Gly Gly Pro Pro Leu Glu Ala Phe Arg Lys Val Ala His Arg
            65                  70                  75

Val Pro Met Met Ser Leu Ala Asn Ala Phe Gly Glu Gly Asp Leu
            80                  85                  90

Arg Asp Phe Asp Arg Arg Val Arg Gln Glu Val Gly Glu Ala Ala
            95                  100                 105

Tyr Val Cys Glu Leu Lys Ile Asp Gly Leu Ala Val Ser Val Arg
            110                 115                 120

Tyr Glu Asp Gly Tyr Phe Val Gln Gly Ala Thr Arg Gly Asp Gly
            125                 130                 135

Thr Thr Gly Glu Asp Ile Thr Glu Asn Leu Lys Thr Ile Arg Ser
            140                 145                 150

Leu Pro Leu Arg Leu Lys Glu Pro Val Ser Leu Glu Ala Arg Gly
            155                 160                 165

Glu Ala Phe Met Pro Lys Ala Ser Phe Leu Arg Leu Asn Glu Glu
            170                 175                 180

-continued

```
Arg Lys Ala Arg Gly Glu Glu Leu Phe Ala Asn Pro Arg Asn Ala
                185                 190                 195

Ala Ala Gly Ser Leu Arg Gln Leu Asp Pro Lys Val Ala Ala Ser
            200                 205                 210

Arg Gln Leu Asp Leu Phe Val Tyr Gly Leu Ala Asp Ala Glu Ala
            215                 220                 225

Leu Gly Ile Ala Ser His Ser Glu Ala Leu Asp Tyr Leu Gln Ala
            230                 235                 240

Leu Gly Phe Lys Val Asn Pro Glu Arg Arg Cys Ala Asn Ile
            245                 250                 255

Asp Glu Val Ile Ala Phe Val Ser Glu Trp His Asp Lys Arg Pro
            260                 265                 270

Gln Leu Pro Tyr Glu Ile Asp Gly Ile Val Ile Lys Val Asp Ser
            275                 280                 285

Phe Ala Gln Gln Arg Ala Leu Gly Ala Thr Ala Lys Ser Pro Arg
            290                 295                 300

Trp Ala Ile Ala Tyr Lys Phe Pro Ala Glu Glu Val Val Thr Thr
            305                 310                 315

Leu Ile Gly Ile Glu Val Asn Val Gly Arg Thr Gly Val Val Thr
            320                 325                 330

Pro Thr Ala Ile Leu Glu Pro Val Arg Val Ala Gly Thr Thr Val
            335                 340                 345

Gln Arg Ala Thr Leu His Asn Glu Asp Phe Ile Arg Glu Lys Asp
            350                 355                 360

Ile Arg Ile Gly Asp Ala Val Ile Ile Lys Lys Ala Gly Asp Ile
            365                 370                 375

Ile Pro Glu Val Val Gly Val Val Asp Arg Arg Asp Gly Asp
            380                 385                 390

Glu Thr Pro Phe Ala Met Pro Thr His Cys Pro Glu Cys Glu Ser
            395                 400                 405

Glu Leu Val Arg Leu Glu Gly Glu Val Ala Leu Arg Cys Leu Asn
            410                 415                 420

Pro Asn Cys Pro Ala Gln Leu
            425

<210> SEQ ID NO 4
<211> LENGTH: 428
<212> TYPE: PRT
<213> ORGANISM: Thermus filiformis
<220> FEATURE:
<221> NAME/KEY: CHAIN
<223> OTHER INFORMATION: N-terminal portion of NAD+-dependent DNA ligase

<400> SEQUENCE: 4

Glu Glu Ala Arg Arg Arg Ile Asn Glu Leu Arg Asp Leu Ile Arg
              5                  10                  15

Tyr His Asn Tyr Arg Tyr Tyr Val Leu Ala Asp Pro Glu Ile Ser
             20                  25                  30

Asp Ala Glu Tyr Asp Arg Leu Leu Arg Glu Leu Lys Glu Leu Glu
             35                  40                  45

Glu Arg Phe Pro Glu Phe Lys Ser Pro Asp Ser Pro Thr Glu Gln
             50                  55                  60

Val Gly Ala Arg Pro Leu Glu Pro Thr Phe Arg Pro Val Arg His
             65                  70                  75

Pro Thr Arg Met Tyr Ser Leu Asp Asn Ala Phe Thr Tyr Glu Glu
```

```
                    80                  85                  90
Val Leu Ala Phe Glu Glu Arg Leu Glu Arg Leu Ala Glu Ala Pro
                95                 100                 105
Ser Leu Tyr Thr Val Glu His Lys Val Asp Gly Leu Ser Val Leu
               110                 115                 120
Tyr Tyr Glu Glu Gly Val Trp Ser Thr Gly Ser Gly Asp Gly Glu
               125                 130                 135
Val Gly Glu Glu Val Thr Gln Asn Leu Leu Thr Ile Pro Thr Ile
               140                 145                 150
Pro Arg Arg Leu Lys Gly Val Pro Asp Arg Leu Glu Val Arg Gly
               155                 160                 165
Glu Val Tyr Met Pro Ile Glu Ala Phe Leu Arg Leu Asn Glu Glu
               170                 175                 180
Leu Glu Glu Arg Gly Glu Lys Val Phe Lys Asn Pro Arg Asn Ala
               185                 190                 195
Ala Ala Gly Ser Leu Arg Gln Lys Asp Pro Arg Val Thr Ala Lys
               200                 205                 210
Arg Gly Leu Arg Ala Thr Phe Tyr Ala Leu Gly Leu Gly Leu Gly
               215                 220                 225
Leu Glu Glu Ser Gly Leu Lys Ser Gln Tyr Glu Leu Leu Leu Trp
               230                 235                 240
Leu Lys Glu Lys Gly Phe Pro Val Glu His Cys Tyr Glu Lys Ala
               245                 250                 255
Leu Gly Ala Glu Gly Val Glu Glu Val Tyr Arg Arg Gly Leu Ala
               260                 265                 270
Gln Arg His Ala Leu Pro Phe Glu Ala Asp Gly Val Val Leu Lys
               275                 280                 285
Leu Asp Asp Leu Thr Leu Trp Gly Glu Leu Gly Tyr Thr Ala Arg
               290                 295                 300
Ala Pro Arg Phe Ala Leu Ala Tyr Lys Phe Pro Ala Glu Glu Lys
               305                 310                 315
Glu Thr Arg Leu Leu Asp Val Val Phe Gln Val Gly Arg Thr Gly
               320                 325                 330
Arg Val Thr Pro Val Gly Val Leu Glu Pro Val Phe Ile Glu Gly
               335                 340                 345
Ser Glu Val Ser Arg Val Thr Leu His Asn Glu Ser Tyr Ile Glu
               350                 355                 360
Glu Leu Asp Ile Arg Ile Gly Asp Trp Val Leu Val His Lys Ala
               365                 370                 375
Gly Gly Val Ile Pro Glu Val Leu Arg Val Leu Lys Glu Arg Arg
               380                 385                 390
Thr Gly Lys Glu Arg Pro Ile Arg Trp Pro Glu Ala Cys Pro Glu
               395                 400                 405
Cys Gly His Arg Leu Val Lys Glu Gly Lys Val His Arg Cys Pro
               410                 415                 420
Asn Pro Leu Cys Pro Ala Lys Arg
               425

<210> SEQ ID NO 5
<211> LENGTH: 52
<212> TYPE: PRT
<213> ORGANISM: Amsacta moorei entomopoxvirus
<220> FEATURE:
<221> NAME/KEY: DOMAIN
<223> OTHER INFORMATION: domain Ia of NAD+-dependent DNA ligase
```

```
<400> SEQUENCE: 5

Asn Asp Leu Glu Asn Ile Ile Gln Thr Leu Asp Asn Ser Tyr Tyr
                 5                   10                  15

Asp Lys Glu Ala Leu Ile Ser Asp Lys Lys Tyr Asp Leu Ile Arg
                20                  25                  30

Asn Phe Ile Asn Asn Lys Tyr Pro Asn Glu Ser Leu Cys Lys Lys
                35                  40                  45

Ile Gly Tyr Thr Pro Glu Asp
                50

<210> SEQ ID NO 6
<211> LENGTH: 52
<212> TYPE: PRT
<213> ORGANISM: Melanoplus sanguinipes entomopoxvirus
<220> FEATURE:
<221> NAME/KEY: DOMAIN
<223> OTHER INFORMATION: domain Ia of NAD+-dependent DNA ligase

<400> SEQUENCE: 6

Glu Asp Ile Ser Glu Ile Ile Lys Ile Leu Asn Glu Lys Tyr Tyr
                 5                   10                  15

Glu Gly Glu Thr Leu Ile Ser Asp Glu Ile Tyr Asp Lys Ile Ile
                20                  25                  30

Glu Tyr Val Asn Lys Lys Tyr Pro Asp Asn Asp Ile Thr Lys Lys
                35                  40                  45

Ile Gly Tyr Glu Pro Lys Asn
                50

<210> SEQ ID NO 7
<211> LENGTH: 60
<212> TYPE: PRT
<213> ORGANISM: Aquifex aeolicus
<220> FEATURE:
<221> NAME/KEY: DOMAIN
<223> OTHER INFORMATION: domain Ia of NAD+-dependent DNA ligase

<400> SEQUENCE: 7

Glu Asp Leu Arg Glu Val Ile Arg Tyr His Asp Tyr Lys Tyr Tyr
                 5                   10                  15

Val Glu Ala Asn Pro Val Ile Pro Asp Tyr Asp Tyr Asp Arg Leu
                20                  25                  30

Phe Arg Ala Leu Lys Glu Ile Glu Lys Lys Tyr Pro Glu Leu Ile
                35                  40                  45

Thr Pro Asp Ser Pro Thr Gln Arg Val Ala Ser Glu Ile Ser Gly
                50                  55                  60

<210> SEQ ID NO 8
<211> LENGTH: 60
<212> TYPE: PRT
<213> ORGANISM: Borrelia burgdorferi
<220> FEATURE:
<221> NAME/KEY: DOMAIN
<223> OTHER INFORMATION: domain Ia of NAD+-dependent DNA ligase

<400> SEQUENCE: 8

Ala Asp Leu Lys Lys Leu Ile Arg Lys Trp Asp Lys Glu Tyr Tyr
                 5                   10                  15

Val Asp Ser Leu Pro Ser Val Glu Asp Phe Val Tyr Asp Lys His
                20                  25                  30

Ile Leu Arg Leu Gln Glu Leu Glu Ser Lys Tyr Pro Glu Tyr Lys
```

```
                    35                  40                  45

Thr Leu Asp Ser Pro Thr Leu Lys Phe Gly Ser Asp Leu Leu Asn
                50                  55                  60

<210> SEQ ID NO 9
<211> LENGTH: 60
<212> TYPE: PRT
<213> ORGANISM: Bordatella pertussis
<220> FEATURE:
<221> NAME/KEY: DOMAIN
<223> OTHER INFORMATION: domain Ia of NAD+-dependent DNA ligase

<400> SEQUENCE: 9

Ala Arg Leu Arg Ala Glu Ile Glu Gln His Asn Ile Arg Tyr Tyr
                 5                  10                  15

Val His Asp Asp Pro Ser Val Pro Asp Ala Glu Tyr Asp Ala Leu
                20                  25                  30

Met Arg Asp Leu Gln Ala Leu Glu Ala Glu His Pro Glu Leu Val
                35                  40                  45

Thr Pro Asp Ser Pro Thr Gln Arg Val Gly Ala Ala Pro Leu Ala
                50                  55                  60

<210> SEQ ID NO 10
<211> LENGTH: 60
<212> TYPE: PRT
<213> ORGANISM: Campylobacter jejuni
<220> FEATURE:
<221> NAME/KEY: DOMAIN
<223> OTHER INFORMATION: domain Ia of NAD+-dependent DNA ligase

<400> SEQUENCE: 10

Leu Glu Lys Val Ala Leu Ala Asn Leu Trp Met Arg Ala Tyr Tyr
                 5                  10                  15

Glu Lys Asp Glu Pro Leu Ala Ser Asp Glu Glu Tyr Asp Ala Leu
                20                  25                  30

Ile Arg Glu Leu Arg Val Phe Glu Glu Gln Asn Lys Asp Glu Ile
                35                  40                  45

Ser Lys Asp Ser Pro Thr Gln Lys Ile Ala Pro Thr Ile Gln Ser
                50                  55                  60

<210> SEQ ID NO 11
<211> LENGTH: 60
<212> TYPE: PRT
<213> ORGANISM: Chlamydia pneumoniae
<220> FEATURE:
<221> NAME/KEY: DOMAIN
<223> OTHER INFORMATION: domain Ia of NAD+-dependent DNA ligase

<400> SEQUENCE: 11

Leu Ala Leu Cys Arg Glu Leu Glu Asp His Asp Tyr Ser Tyr Tyr
                 5                  10                  15

Val Leu His Arg Pro Arg Ile Ser Asp Tyr Glu Tyr Asp Met Lys
                20                  25                  30

Leu Arg Lys Leu Leu Glu Ile Glu Arg Ser His Pro Glu Trp Lys
                35                  40                  45

Val Leu Trp Ser Pro Ser Thr Arg Leu Gly Asp Arg Pro Ser Gly
                50                  55                  60

<210> SEQ ID NO 12
<211> LENGTH: 60
<212> TYPE: PRT
<213> ORGANISM: Chlamydia trachomatis
```

```
<220> FEATURE:
<221> NAME/KEY: DOMAIN
<223> OTHER INFORMATION: domain Ia of NAD+-dependent DNA ligase

<400> SEQUENCE: 12

Ile Ala Leu Cys Thr Glu Leu Val Glu His Asp Arg Arg Tyr Tyr
                 5                  10                  15

Val Leu Asn Gln Pro Thr Ile Ser Asp Tyr Ser Tyr Asp Val Lys
             20                  25                  30

Met Arg Glu Leu Gln Glu Ile Glu Val Gln His Pro Glu Trp Lys
             35                  40                  45

Val Ser Trp Ser Pro Thr Met Tyr Leu Gly Asp Arg Pro Ser Gly
             50                  55                  60

<210> SEQ ID NO 13
<211> LENGTH: 60
<212> TYPE: PRT
<213> ORGANISM: Deinococcus radiodurans
<220> FEATURE:
<221> NAME/KEY: DOMAIN
<223> OTHER INFORMATION: domain Ia of NAD+-dependent DNA ligase

<400> SEQUENCE: 13

Leu Ala Leu Arg Asp Glu Val Ala Leu His Asn Arg Ala Tyr Tyr
                 5                  10                  15

Glu Gln Asp Ala Pro Thr Ile Pro Asp Asp Glu Tyr Asp Arg Leu
             20                  25                  30

Ala Arg Glu Leu Arg Glu Leu Glu Ala Ala His Pro Glu Phe Ala
             35                  40                  45

Asp Asp His Ser Pro Val Gln Thr Val Gly Gly Ala Pro Ser Ser
             50                  55                  60

<210> SEQ ID NO 14
<211> LENGTH: 60
<212> TYPE: PRT
<213> ORGANISM: E. coli
<220> FEATURE:
<221> NAME/KEY: DOMAIN
<222> LOCATION: 9.....68
<223> OTHER INFORMATION: domain Ia of NAD+-dependent DNA ligase

<400> SEQUENCE: 14

Thr Glu Leu Arg Thr Thr Leu Arg His His Glu Tyr Leu Tyr His
                 5                  10                  15

Val Met Asp Ala Pro Glu Ile Pro Asp Ala Glu Tyr Asp Arg Leu
             20                  25                  30

Met Arg Glu Leu Arg Glu Leu Glu Thr Lys His Pro Glu Leu Ile
             35                  40                  45

Thr Pro Asp Ser Pro Thr Gln Arg Val Gly Ala Ala Pro Leu Ala
             50                  55                  60

<210> SEQ ID NO 15
<211> LENGTH: 60
<212> TYPE: PRT
<213> ORGANISM: Geobacter sulfurreducens
<220> FEATURE:
<221> NAME/KEY: DOMAIN
<223> OTHER INFORMATION: domain Ia of NAD+-dependent DNA ligase

<400> SEQUENCE: 15

Ala Ala Leu Arg Thr Glu Leu Glu Arg His Asn Arg Leu Tyr Tyr
                 5                  10                  15
```

```
Ala Glu Asp Arg Pro Glu Ile Thr Asp Ala Glu Tyr Asp Leu Leu
                20                  25                  30

Phe Arg Glu Leu Val Asp Leu Glu Thr Arg Phe Pro Asp Leu Ala
                35                  40                  45

Ala Pro Asp Ser Pro Thr Gln Arg Val Gly Gly Ala Pro Leu Asp
                50                  55                  60

<210> SEQ ID NO 16
<211> LENGTH: 60
<212> TYPE: PRT
<213> ORGANISM: Haemophilus influenzae
<220> FEATURE:
<221> NAME/KEY: DOMAIN
<223> OTHER INFORMATION: domain Ia of NAD+-dependent DNA ligase

<400> SEQUENCE: 16

Asp Asn Leu Arg Lys Thr Leu Arg Gln Tyr Glu Tyr Glu Tyr His
                 5                  10                  15

Val Leu Asp Asn Pro Ser Val Pro Asp Ser Glu Tyr Asp Arg Leu
                20                  25                  30

Phe His Gln Leu Lys Ala Leu Glu Leu Glu His Pro Glu Phe Leu
                35                  40                  45

Thr Ser Asp Ser Pro Thr Gln Arg Val Gly Ala Lys Pro Leu Ser
                50                  55                  60

<210> SEQ ID NO 17
<211> LENGTH: 60
<212> TYPE: PRT
<213> ORGANISM: Lactococcus lactis
<220> FEATURE:
<221> NAME/KEY: DOMAIN
<223> OTHER INFORMATION: domain Ia of NAD+-dependent DNA ligase

<400> SEQUENCE: 17

Lys Glu Leu Thr Glu Lys Leu Asn Gln Tyr Ala Tyr Glu Tyr Tyr
                 5                  10                  15

Thr Leu Asp Glu Pro Ser Val Glu Asp Ser Glu Tyr Asp Arg Leu
                20                  25                  30

Tyr Gln Glu Leu Val Lys Leu Glu Ala Glu Asn Pro Gln Leu Thr
                35                  40                  45

Arg Ala Asp Ser Pro Thr His Arg Thr Gly Gly Val Ile Leu Asp
                50                  55                  60

<210> SEQ ID NO 18
<211> LENGTH: 60
<212> TYPE: PRT
<213> ORGANISM: Legionella pneumophila
<220> FEATURE:
<221> NAME/KEY: DOMAIN
<223> OTHER INFORMATION: domain Ia of NAD+-dependent DNA ligase

<400> SEQUENCE: 18

Glu Thr Leu Lys Glu Gln Ile Arg Lys Tyr Asp Tyr His Tyr Tyr
                 5                  10                  15

Val Leu Asp Glu Pro Leu Val Pro Asp Ala Glu Tyr Asp Arg Cys
                20                  25                  30

Phe Lys Ala Leu Gln Gln Tyr Glu Glu Gln Tyr Pro Gln Phe Leu
                35                  40                  45

Ser Pro Asp Ser Pro Thr Gln Arg Val Ser Gly Thr Pro Ser Asp
                50                  55                  60
```

```
<210> SEQ ID NO 19
<211> LENGTH: 60
<212> TYPE: PRT
<213> ORGANISM: Mycoplasma genitalia
<220> FEATURE:
<221> NAME/KEY: DOMAIN
<223> OTHER INFORMATION: domain Ia of NAD+-dependent DNA ligase

<400> SEQUENCE: 19

Gln Gln Leu Val Asn Leu Ile Lys Asn Tyr Asp Tyr His Tyr Tyr
                 5                  10                  15

Val Leu Ser Glu Pro Leu Ile Asp Asp Phe Glu Tyr Asp Met Leu
                20                  25                  30

Tyr Lys Ser Leu Gln Gln Leu Glu Lys Asp His Pro Asp Leu Ile
                35                  40                  45

Gln Ile Asp Ser Pro Thr Gln Arg Val Gly Gly Glu Ala Val Lys
                50                  55                  60

<210> SEQ ID NO 20
<211> LENGTH: 60
<212> TYPE: PRT
<213> ORGANISM: Mycobacterium leprae
<220> FEATURE:
<221> NAME/KEY: DOMAIN
<223> OTHER INFORMATION: domain Ia of NAD+-dependent DNA ligase

<400> SEQUENCE: 20

Arg Lys Leu Thr Glu Glu Val Arg Glu His Gln Phe Arg Tyr Tyr
                 5                  10                  15

Val Arg Asp Ala Pro Ile Ile Ser Asp Ala Glu Phe Asp Ala Leu
                20                  25                  30

Leu Asp Arg Leu Thr Val Leu Glu Glu Gln His Pro Glu Leu Cys
                35                  40                  45

Thr Pro Asp Ser Pro Thr Gln Leu Val Gly Gly Ala Gly Phe Met
                50                  55                  60

<210> SEQ ID NO 21
<211> LENGTH: 60
<212> TYPE: PRT
<213> ORGANISM: Mycoplasma pneumoniae
<220> FEATURE:
<221> NAME/KEY: DOMAIN
<223> OTHER INFORMATION: domain Ia of NAD+-dependent DNA ligase

<400> SEQUENCE: 21

Arg Ala Ile Val Glu Gln Leu Lys Arg Tyr Asp Tyr His Tyr Tyr
                 5                  10                  15

Val Leu Asp Asp Pro Leu Val Ser Asp Phe Glu Tyr Asp Gln Leu
                20                  25                  30

Tyr Lys Gln Leu Gln Ala Leu Glu Gln Ala His Pro Glu Leu Ile
                35                  40                  45

Gln Pro Asp Ser Pro Thr Gln Arg Val Gly Gly Ile Val Val Glu
                50                  55                  60

<210> SEQ ID NO 22
<211> LENGTH: 60
<212> TYPE: PRT
<213> ORGANISM: Mycobacterium tuberculosis
<220> FEATURE:
<221> NAME/KEY: DOMAIN
<223> OTHER INFORMATION: domain Ia of NAD+-dependent DNA ligase

<400> SEQUENCE: 22
```

```
Gln Ala Leu Ala Glu Glu Val Arg Glu His Gln Phe Arg Tyr Tyr
                5                  10                  15

Val Arg Asp Ala Pro Ile Ile Ser Asp Ala Glu Phe Asp Glu Leu
               20                  25                  30

Leu Arg Arg Leu Glu Ala Leu Glu Glu Gln His Pro Glu Leu Arg
               35                  40                  45

Thr Pro Asp Ser Pro Thr Gln Leu Val Gly Gly Ala Gly Phe Ala
               50                  55                  60
```

<210> SEQ ID NO 23
<211> LENGTH: 60
<212> TYPE: PRT
<213> ORGANISM: Neisseria meningitidis
<220> FEATURE:
<221> NAME/KEY: DOMAIN
<223> OTHER INFORMATION: domain Ia of NAD+-dependent DNA ligase

<400> SEQUENCE: 23

```
Cys Arg Leu Thr Asp Leu Leu Asn Arg Tyr Ala Tyr Glu Tyr Tyr
                5                  10                  15

Thr Leu Asp Ala Pro Ser Val Pro Asp Ala Glu Tyr Asp Lys Leu
               20                  25                  30

Phe Arg Glu Leu Glu Ala Leu Glu Leu Asn His Pro Glu Leu Lys
               35                  40                  45

Leu Pro Asp Ser Pro Thr Gln Arg Val Gly Gly Glu Pro Leu Ala
               50                  55                  60
```

<210> SEQ ID NO 24
<211> LENGTH: 60
<212> TYPE: PRT
<213> ORGANISM: Pseudoalteromonas haloplanktis
<220> FEATURE:
<221> NAME/KEY: DOMAIN
<223> OTHER INFORMATION: domain Ia of NAD+-dependent DNA ligase

<400> SEQUENCE: 24

```
Asn His Leu Arg Ile Ile Leu Glu Gln His Asn Tyr Asn Tyr Tyr
                5                  10                  15

Val Leu Asp Thr Pro Ser Ile Pro Asp Ser Glu Tyr Asp Arg Leu
               20                  25                  30

Leu Arg Glu Leu Ser Ala Leu Glu Thr Glu His Pro Glu Phe Leu
               35                  40                  45

Thr Ala Asp Ser Pro Thr Gln Lys Val Gly Gly Ala Ala Leu Ser
               50                  55                  60
```

<210> SEQ ID NO 25
<211> LENGTH: 60
<212> TYPE: PRT
<213> ORGANISM: Pseudomonas putida
<220> FEATURE:
<221> NAME/KEY: DOMAIN
<223> OTHER INFORMATION: domain Ia of NAD+-dependent DNA ligase

<400> SEQUENCE: 25

```
Leu Glu Leu Arg Ala Glu Leu Asp Gln His Asn Tyr Arg Tyr Tyr
                5                  10                  15

Val Leu Asp Glu Pro Ser Val Pro Asp Ala Glu Tyr Asp Arg Leu
               20                  25                  30

Phe Asn Glu Leu Lys Ala Leu Glu Ala Glu His Pro His Leu Val
               35                  40                  45

Thr Pro Asp Ser Pro Thr Gln Arg Val Gly Gly Ala Ala Leu Ala
```

<210> SEQ ID NO 26
<211> LENGTH: 60
<212> TYPE: PRT
<213> ORGANISM: Rhodothermus marinus
<220> FEATURE:
<221> NAME/KEY: DOMAIN
<223> OTHER INFORMATION: domain Ia of NAD+-dependent DNA ligase

<400> SEQUENCE: 26

Ala Arg Leu Arg Glu Val Leu Asn Gln His Ala Tyr Arg Tyr Tyr
                5                   10                  15

Val Leu Asp Asn Pro Leu Ile Pro Asp Ala Asp Tyr Asp Leu Leu
            20                  25                  30

Met Gln Ala Leu Arg Lys Leu Glu Ala Arg Phe Pro Glu Leu Val
            35                  40                  45

Thr Pro Asp Ser Pro Thr Gln Arg Val Gly Gly Pro Pro Leu Gly
            50                  55                  60

<210> SEQ ID NO 27
<211> LENGTH: 60
<212> TYPE: PRT
<213> ORGANISM: Rickettsia prowazekii
<220> FEATURE:
<221> NAME/KEY: DOMAIN
<223> OTHER INFORMATION: domain Ia of NAD+-dependent DNA ligase

<400> SEQUENCE: 27

Lys Glu Leu Ala Asp Lys Ile Ala Met Tyr Asn His Ala Tyr Tyr
                5                   10                  15

Ile Glu Asp Asn Pro Leu Val Ser Asp Ser Glu Tyr Asp Gln Leu
            20                  25                  30

Phe Asn Ile Asn Leu Lys Leu Glu Asn Thr Phe Pro His Leu Val
            35                  40                  45

Leu Ser Asn Ser Pro Ser Lys Lys Val Gly Ala Asn Ile Thr Asn
            50                  55                  60

<210> SEQ ID NO 28
<211> LENGTH: 60
<212> TYPE: PRT
<213> ORGANISM: Staphylococcus aureus
<220> FEATURE:
<221> NAME/KEY: DOMAIN
<223> OTHER INFORMATION: domain Ia of NAD+-dependent DNA ligase

<400> SEQUENCE: 28

Asn Glu Leu His Asp Leu Leu Asn Gln Tyr Ser Tyr Glu Tyr Tyr
                5                   10                  15

Val Glu Asp Asn Pro Ser Val Pro Asp Ser Glu Tyr Asp Lys Leu
            20                  25                  30

Leu His Glu Leu Ile Lys Ile Glu Glu His Pro Glu Tyr Lys
            35                  40                  45

Thr Val Asp Ser Pro Thr Val Arg Val Gly Gly Glu Ala Gln Ala
            50                  55                  60

<210> SEQ ID NO 29
<211> LENGTH: 60
<212> TYPE: PRT
<213> ORGANISM: Streptococcus mutans
<220> FEATURE:
<221> NAME/KEY: DOMAIN
<223> OTHER INFORMATION: domain Ia of NAD+-dependent DNA ligase

```
<400> SEQUENCE: 29

Asn Glu Leu Val Gln Leu Leu Asn Gln Tyr Ala Arg Glu Tyr Tyr
                 5                  10                  15

Thr Lys Asp Asn Pro Ser Val Ser Asp Ala Glu Tyr Asp Lys Leu
             20                  25                  30

Tyr Arg Glu Leu Val Glu Leu Glu Lys Glu Phe Pro Glu Asp Ile
             35                  40                  45

Leu Pro Asn Ser Pro Thr His Arg Val Gly Asp Leu Val Leu Asp
             50                  55                  60

<210> SEQ ID NO 30
<211> LENGTH: 60
<212> TYPE: PRT
<213> ORGANISM: Thiobacillus ferrooxidans
<220> FEATURE:
<221> NAME/KEY: DOMAIN
<223> OTHER INFORMATION: domain Ia of NAD+-dependent DNA ligase

<400> SEQUENCE: 30

Gln Gln Leu Arg Ala Glu Leu Val Ala Ala Asn Asn Ala Tyr Tyr
                 5                  10                  15

Arg Glu Asp Ser Pro Thr Leu Ser Asp Ala Glu Tyr Asp Ala Arg
             20                  25                  30

Leu Arg Glu Leu Arg Thr Leu Glu Asp Arg Asn Pro Gln Trp Gln
             35                  40                  45

Ser Ala Asp Ser Pro Thr Gln Arg Val Gly Ala Ala Pro Val Glu
             50                  55                  60

<210> SEQ ID NO 31
<211> LENGTH: 60
<212> TYPE: PRT
<213> ORGANISM: Zymomonas mobilis
<220> FEATURE:
<221> NAME/KEY: DOMAIN
<223> OTHER INFORMATION: domain Ia of NAD+-dependent DNA ligase

<400> SEQUENCE: 31

Glu Arg Leu Ala Lys Leu Ile Ser His Tyr Asp His Leu Tyr His
                 5                  10                  15

Asp Lys Asp Asn Pro Ala Val Pro Asp Ser Glu Tyr Asp Ala Leu
             20                  25                  30

Val Leu Arg Asn Arg Arg Ile Glu Gln Phe Phe Pro Asp Leu Ile
             35                  40                  45

Arg Pro Asp Ser Pro Ser Lys Lys Val Gly Ser Arg Pro Asn Ser
             50                  55                  60

<210> SEQ ID NO 32
<211> LENGTH: 60
<212> TYPE: PRT
<213> ORGANISM: Bacillus stearothermophilus
<220> FEATURE:
<221> NAME/KEY: DOMAIN
<223> OTHER INFORMATION: domain Ia of NAD+-dependent DNA ligase

<400> SEQUENCE: 32

Ala Glu Leu Arg Glu Leu Leu Asn Arg Tyr Gly Tyr Glu Tyr Tyr
                 5                  10                  15

Val Leu Asp Arg Pro Ser Val Pro Asp Ala Glu Tyr Asp Arg Leu
             20                  25                  30

Met Gln Glu Leu Ile Ala Ile Glu Glu Gln Tyr Pro Glu Leu Lys
```

-continued

```
                    35                  40                  45
Thr Ser Asp Ser Pro Thr Gln Arg Ile Gly Gly Pro Pro Leu Glu
         50                  55                  60

<210> SEQ ID NO 33
<211> LENGTH: 60
<212> TYPE: PRT
<213> ORGANISM: Thermus filiformis
<220> FEATURE:
<221> NAME/KEY: DOMAIN
<223> OTHER INFORMATION: domain Ia of NAD+-dependent DNA ligase

<400> SEQUENCE: 33

Asn Glu Leu Arg Asp Leu Ile Arg Tyr His Asn Tyr Arg Tyr Tyr
 1               5                  10                  15

Val Leu Ala Asp Pro Glu Ile Ser Asp Ala Glu Tyr Asp Arg Leu
             20                  25                  30

Leu Arg Glu Leu Lys Glu Leu Glu Glu Arg Phe Pro Glu Phe Lys
         35                  40                  45

Ser Pro Asp Ser Pro Thr Glu Gln Val Gly Ala Arg Pro Leu Glu
     50                  55                  60

<210> SEQ ID NO 34
<211> LENGTH: 36
<212> TYPE: DNA
<213> ORGANISM: Artificial sequence
<220> FEATURE:
<223> OTHER INFORMATION: nicked duplex substrate used in ligation
      reactions

<400> SEQUENCE: 34
catatccgtg tcgcccttat tccgatagtg actaca                         36

<210> SEQ ID NO 35
<211> LENGTH: 36
<212> TYPE: DNA
<213> ORGANISM: Artificial sequence
<220> FEATURE:
<223> OTHER INFORMATION: nicked duplex substrate used in ligation
      reactions

<400> SEQUENCE: 35
gtataggcac agcgggaata aggctatcac tgatgt                         36

<210> SEQ ID NO 36
<211> LENGTH: 6
<212> TYPE: PRT
<213> ORGANISM: Amsacta moorei entomopoxvirus
<220> FEATURE:
<221> NAME/KEY: CHAIN
<222> LOCATION: -1....5
<223> OTHER INFORMATION: proteolytic product of NAD+-dependent DNA
      ligase from Amsacta moorei entomopoxvirus, X = met

<400> SEQUENCE: 36

His Xaa Asn His Ile Lys
             5

<210> SEQ ID NO 37
<211> LENGTH: 6
<212> TYPE: PRT
<213> ORGANISM: Amsacta moorei entomopoxvirus
<220> FEATURE:
<221> NAME/KEY: CHAIN
<223> OTHER INFORMATION: proteolytic product of NAD+-dependent DNA
      ligase from Amsacta moorei entomopoxvirus
```

-continued

```
<400> SEQUENCE: 37

Ile Gly Tyr Thr Pro Glu
                5

<210> SEQ ID NO 38
<211> LENGTH: 6
<212> TYPE: PRT
<213> ORGANISM: Amsacta moorei entomopoxvirus
<220> FEATURE:
<221> NAME/KEY: CHAIN
<223> OTHER INFORMATION: proteolytic product of NAD+-dependent DNA
      ligase from Amsacta moorei entomopoxvirus

<400> SEQUENCE: 38

Lys Ile Gly Tyr Thr Pro
                5

<210> SEQ ID NO 39
<211> LENGTH: 6
<212> TYPE: PRT
<213> ORGANISM: Artificial sequence
<220> FEATURE:
<221> NAME/KEY: CHAIN
<223> OTHER INFORMATION: a histine tag

<400> SEQUENCE: 39

Gly His His His His His
                5

<210> SEQ ID NO 40
<211> LENGTH: 6
<212> TYPE: PRT
<213> ORGANISM: Amsacta moorei entomopoxvirus
<220> FEATURE:
<221> NAME/KEY: CHAIN
<223> OTHER INFORMATION: proteolytic product of NAD+-dependent DNA
      ligase from Amsacta moorei entomopoxvirus

<400> SEQUENCE: 40

Asn Ser Ile Arg Thr Val
                5

<210> SEQ ID NO 41
<211> LENGTH: 6
<212> TYPE: PRT
<213> ORGANISM: Amsacta moorei entomopoxvirus
<220> FEATURE:
<221> NAME/KEY: CHAIN
<223> OTHER INFORMATION: proteolytic product of NAD+-dependent DNA
      ligase from Amsacta moorei entomopoxvirus

<400> SEQUENCE: 41

Asn Ser Ile Arg Thr Val
                5
```